US008623279B2

(12) United States Patent
Malik et al.

(10) Patent No.: US 8,623,279 B2
(45) Date of Patent: Jan. 7, 2014

(54) IONIC LIQUID MEDIATED SOL-GEL SORBENTS

(75) Inventors: Abdul Malik, Tampa, FL (US); Anne M. Shearrow, Lithia, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/300,943

(22) Filed: Nov. 21, 2011

(65) Prior Publication Data

US 2012/0128551 A1 May 24, 2012

Related U.S. Application Data

(63) Continuation of application No. PCT/US2010/035797, filed on May 21, 2010.

(60) Provisional application No. 61/180,274, filed on May 21, 2009.

(51) Int. Cl.
*G01N 30/60* (2006.01)

(52) U.S. Cl.
USPC ............. 422/70; 73/23.39; 73/61.53; 95/101; 95/108; 95/154; 210/198.2; 422/69; 422/89; 422/527

(58) Field of Classification Search
USPC ............ 422/69, 70, 89, 527; 73/23.39, 61.53; 210/198.2; 95/101, 108, 154
See application file for complete search history.

(56) References Cited

U.S. PATENT DOCUMENTS

| 2006/0013981 A1 | 1/2006 | Malik et al. |
| 2006/0113231 A1 | 6/2006 | Malik |
| 2007/0095736 A1 | 5/2007 | Malik et al. |
| 2007/0172960 A1 | 7/2007 | Malik et al. |
| 2008/0245186 A1 | 10/2008 | Yang et al. |

OTHER PUBLICATIONS

J. Pawliszyn, S. Liu, Sample Introduction for Capillary Gas Chromatography with Laser Desorption and Optical Fibers, Anal. Chem. 59 (1987) 1475-1478.

R. Eisert, J. Pawliszyn, Automated In-Tube Solid-Phase Microextraction Coupled to High-Performance Liquid Chromatography, Anal. Chem. 69 (1997) 3140-3147.

M. E. McComb, R. D. Oleschuk, E. Giller, H. D. Gesser, Microextraction of Volatile Organic Compounds Using the Inside Needle Capillary Adsorption Trap (INCAT) Device, Talanta 44 (1997) 2137-2143.

(Continued)

*Primary Examiner* — Jan Ludlow
(74) *Attorney, Agent, or Firm* — Robert J. Varkonyi; Smith & Hopen, P.A.

(57) ABSTRACT

Ionic liquid (IL)-mediated sol-gel hybrid organic-inorganic materials present enormous potential for effective use in analytical microextraction. One obstacle to materializing this prospect arises from high viscosity of ILs significantly slowing down sol-gel reactions. A method was developed which provides phosphonium-based, pyridinium-based, and imidazolium-based IL-mediated advanced sol-gel organic-inorganic hybrid materials for capillary microextraction. Scanning electron microscopy results demonstrate that ILs can serve as porogenic agents in sol-gel reactions. IL-mediated sol-gel coatings prepared with silanol-terminated polymers provided up to 28 times higher extractions compared to analogous sol-gel coatings prepared without any IL in the sol solution. This study shows that IL-generated porous morphology alone is not enough to provide effective extraction media: careful choice of the organic polymer and the precursor with close sol-gel reactivity must be made to ensure effective chemical bonding of the organic polymer to the created sol-gel material to be able to provide the desired sorbent characteristics.

8 Claims, 14 Drawing Sheets

(56) References Cited

OTHER PUBLICATIONS

H. Kataoka, J. Pawliszyn, Development of In-Tube Solid-Phase Microextraction/Liquid Chromatography/Electrospray Ionization Mass Spectrometry for the Analysis of Mutagenic Heterocyclic Amines, Chromatographia 50 No. 9/10 (1999) 532-538.

S. Bigham, J. Medlar, A. Kabir, C. Shende, A. Alli, A. Malik, Sol-Gel Capillary Microextraction, Anal. Chem. 74 (2002) 752-761.

H. Lord, J. Pawliszyn, Evolution of Solid-Phase Microextraction Technology, J. Chromatogr. A 885 (2000) 153-193.

S. A. Forsyth, J. M. Pringle, D. R. MacFarlane, Ionic Liquids-An Overview, Aust. J. Chem. 57 (2004) 113-119.

N. V. Plechkova, K. R. Seddon, Applications of Ionic Liquids in the Chemical Industry, Chem. Soc. Rev. 37 (2008) 123-150.

S. Chowdhury, R. S. Mohan, J. L. Scott, Reactivity of Ionic Liquids, Tetrahedron 63 (2007) 2363-2389.

A. M. Stalcup, In Ionic Liquids in Chemical Analysis; Ionic Liquids in Liquid Chromatography, M. Koel, M. Ed.; CRC Press: Boca Raton, FL (2009) 168-183.

Wang et al., Sol-Gel Column Technology for Single-Step Deactivation, Coating, and Stationary-Phase Immobilization in High-Resolution Capillary Gas Chromatography, Anal. Chem., 69 (1997) 4566-4576.

H. Weingartner, Understanding Ionic Liquids at the Molecular Level: Facts, Problems, and Controversies, Angew. Chem. Int. Ed. 47 (2008) 654-670.

D. W. Armstrong, L. F. He, Y. S. Liu, Examination of Ionic Liquids and Their Interaction with Molecules, When Used as Stationary Phases in Gas Chromatography, Anal. Chem. 71 (1999) 3873-3876.

J. L. Anderson, Ionic Liquids as Stationary Phases in Gas Chromatography, in Ionic Liquids in Chemical Analysis; M. Koel, Ed.; CRC Press: Boca Raton, FL (2009) 139-165.

L. J. He, W. Z. Zhang, L. Zhao, X. Liu, S. X. Jiang, Effect of 1-alkyl-3-methylimidazolium-based Ionic Liquids as the Eluent on the Separation of Ephedrines by Liquid Chromatography, J. Chromatogr. A 1007 (2003) 39-45.

R. Kaliszan, M. P. Marszall, M. J. Markuszewski, T. Baczek, J. Pernak, Suppression of deleterious effects of free silanols in liquid chromatography by imidazolium tetrafluoroborate ionic liquids, J. Chromatogr. A 1030 (2004) 263-271.

M. P. Marszall, R. Kaliszan, Application of Ionic Liquids in Liquid Chromatography, Crit. Rev. Anal. Chem. 37 (2) (2007) 127-140.

Castello &. D'Amato, Evaluation of the Properties of Polyethylene Glycols as Stationary Phases in Gas-Liquid Chromatography, J. Chromatogr. 90 (1974) 291-301.

A. Berthod, S. Carda-Broch, Use of the ionic liquid 1-butyl-3-methylimidazolium hexafluorophosphate in countercurrent chromatography, Anal. Bioanal. Chem. 380 (2004) 168-177.

C. D. Tran, Ionic Liquids for and by Analytical Spectroscopy, Anal. Lett. 40 (13) (2007) 2447-2464.

S. Dai, Y. H. Ju, H. J. Gao, J. S. Lin, S. J. Pennycook, C. E. Barnes, Preparation of silica aerogel using ionic liquids as solvents, Chem. Commun. 3 (2000) 243-244.

Y. Zhou, J. H. Schattka, M. Antonietti, Room-Temperature Ionic Liquids as Template to Monolithic Mesoporous Silica with Wormlike Pores via a Sol-Gel Nanocasting Technique, Nano Lett. 4 (3) (2004) 477-481.

Y. Liu, M. J. Wang, J. Li, Z. Y. Li, P. He, H. T. Liu, J. H. Li, Highly active horseradish peroxidase immobilized in 1-butyl-3-methylimidazolium tetrafluoroborate room-temperature ionic liquid based sol-gel host materials, Chem. Commun. 13 (2005) 1778-1780.

M. A. Klingshim, S. K. Spear, J. D. Holbrey, R. D. Rogers, Ionic liquids as solvent and solvent additives for the synthesis of sol-gel materials, J. Mater. Chem. 15 ( 2005) 5174-5180.

H. F. Wang, Y. Z. Zhu, X. P. Yan, R. Y. Gao, J. Y. Zheng, A Room Temperature Ionic Liquid (RTIL)-Mediated, Non-Hydrolytic Sol-Gel Methodology to Prepare Molecularly Imprinted, Silica-Based Hybrid Monoliths for Chiral Separation, Adv. Mater. 18 (2006) 3266-3270.

A. Karout, A. C. Pierre, Silica xerogels and aerogels synthesized with ionic liquids, J. Non-Cryst. Solids 353 (2007) 2900-2909.

H. F. Wang, Y. Z. Zhu, J. P. Lin, X. P. Yan, Fabrication of molecularly imprinted hybrid monoliths via a room temperature ionic liquid-mediated nonhydrolytic sol-gel route for chiral separation of zolmitriptan by capillary electrochromatography, Electrophoresis 29 (2008) 952-959.

C. J. Adams, A. E. Bradley, K. R. Seddon, The Synthesis of Mesoporous Materials Using Novel Ionic Liquid Templates in Water, Aust. J. Chem. 54 (2001) 679-681.

S. W. Li, Z. Zhou, M. L. Liu, W. Li, J. Ukai, K. Hase, M. Nakanishi, Synthesis and properties of imidazole-grafted hybrid inorganic-organic polymer membranes, Electrochim. Acta 51 (2006) 1351-1358.

Silva & Augusto, Highly porous solid-phase microextraction fiber coating based on poly(ethylene glycol)-modified ormosils synthesized by sol-gel technology, J. Chromatogr. A 1072 (2005) 7-12.

Bagheri, et al., Sol-gel-based solid-phase microextraction and gas chromatography-massspectrometry determination of dextromethorphan and dextrorphan in human plasma, J. Chromatogr. B 818 (2005) 147-157.

Kulkarni, et al., Sol-gel immobilized short-chain poly(ethylene glycol) coating for capillary microextraction of underivatized polar analytes, J. Chromatogr. A 1174 (2007) 50-62.

Wasserscheid & Keim, Ionic Liquids—New "Solutions" for Transition Metal Catalysis, Angew. Chem. Int. Ed. Engl. 2000 , 39, 3772-3789.

Hayes & Malik, Sol-gel chemistry-based Ucon-coated columns for capillary electrophoresis, J. Chromatogr. B 695 (1997) 3-13.

Liu, et al., J. Chen, The preparation of sol-gel materials doped with ionic liquids and trialkyl phosphine oxides for Yttrium(III) uptake, Anal. Chim. Acta 604 (2007) 107-113.

He, et al., Molecularly imprinted silica prepared with immiscible ionic liquid as solvent and porogen for selective recognition of testosterone, Talanta 74 (2008) 1126-1131.

Donato, et al. Synthesis of silica xerogels with highly distinct morphologies in the presence of imidazolium ionic liquids, J. Sol-Gel Sci. Technol. 49 (2009) 71-77.

Chan, et al., The Synthesis and Thermolysis of Imidazole Quaternary Salts, Aust. J. Chem. 30 (1977) 2005-2013.

Bondi, van der Waals Volumes and Radii, J. Phys. Chem. 68 (3) (1964) 441-451.

IONIC LIQUID MEDIATED SOL-GEL SORBENTS

CROSS REFERENCE TO RELATED APPLICATIONS

This application is a continuation of prior filed International Application, Serial Number PCT US2010 035797 filed May 21, 2010, which claims priority to U.S. provisional patent application No. 61/180,274 filed May 21, 2009 which is hereby incorporated by reference into this disclosure.

STATEMENT OF GOVERNMENT INTEREST

This invention was made with government support under Grant No. DGE-0221681 awarded by the National Science Foundation and Grant No. DE-AC05-000R22750 awarded by the Department of Homeland Security. The government has certain rights in the invention.

FIELD OF INVENTION

This invention relates to the creation of ionic liquid sorbents. Specifically, the invention provides a hybrid organic-inorganic sol-gel sorbent.

BACKGROUND OF THE INVENTION

Hydrophilic polar analytes are notoriously difficult to extract and preconcentrate from aqueous matrices. Sample preconcentration is of utmost importance in the trace analysis of these recalcitrant analytes. A variety of extraction-based preconcentration techniques have been utilized for this purpose (Fontanals, R. M. Marce, F. Borrull, J. Chromatogr. A 1152 (2007) 14). With the current trend of miniaturization in analytical instrumentation, microextraction techniques are gaining popularity. Microextraction techniques include solid phase microextraction (SPME) (Pawliszyn, S. Liu, Anal. Chem. 59 (1987) 1475; Belardi, J. Pawliszyn, Water Pollut. Res. J. Can. 24 (1989) 179), hollow fiber microextraction (Zhang, J. Poerschmann, J. Pawliszyn, Anal. Commun. 33 (1996) 219), single-drop microextraction (Jeannot, F. F. Cantwell, Anal. Chem. 69 (1997) 235), liquid phase microextraction (He, H. K. Lee, Anal. Chem. 69 (1997) 4634), extraction techniques based on suspended particles, membranes disks, coated vessel walls, etc. (Lord, J. Pawliszyn, J. Chromatogr. A 885 (2000) 153), and stir bar sorptive extraction (SBSE) (Baltussen, P. Sandra, F. David, C. Cramers, J. Microcolumn Sep. 11 (1999) 737). SPME techniques include traditional fiber SPME (Pawliszyn & Liu, Anal. Chem. 59 (1987) 1475; Belardi & Pawliszyn, Water Pollut. Res. J. Can. 24 (1989) 179; Arthur & Pawliszyn, Anal. Chem. 62 (1990) 2145) and in-tube SPME (Eisert & Pawliszyn, Anal. Chem. 69 (1997) 3140; McComb, et al., Talanta 44 (1997) 2137; Hartmann, et al., Bull. 7 (1998) 96; Kataoka &Pawliszyn, Chromatographia 50 (1999) 532).

In particular, fiber SPME and in-tube SPME (Eisert, J. Pawliszyn, Anal. Chem. 69 (1997) 3140; McComb, R. D. Oleschuk, E. Giller, H. D. Gesser, Talanta 44 (1997) 2137; Hartmann, J. Burhenne, M. Spiteller, Fresenius Environ. Bull. 7 (1998) 96) capillary microextraction (CME) (S. Bigham, J. Medlar, A. Kabir, C. Shende, A. Alli, A. Malik, Anal. Chem. 74 (2002) 752) have experienced an explosive growth over the past two decades, due in part to research by Pawliszyn and co-workers (Pawliszyn & Liu, Anal. Chem. 59 (1987) 1475) which provided a significant step toward automation of sample preparation in chemical analysis. Another significant reason behind such growth lies in the fact that these techniques pose little risk to human health and the environment by completely eliminating the use of organic solvents in the extraction process. Moreover, CME uses a sorbent coating located inside a small diameter tubing either in the form of a surface coating or a packed monolithic sorbent bed. Thus, analytes are directly extracted onto the sorbent coating bed from a sample as they pass through the tubing (Eisert, J. Pawliszyn, Anal. Chem. 69 (1997) 3140).

In addition to its use in GC, (Arthur, et al., Anal. Chem. 64 (1992) 1960), high-performance liquid chromatography (HPLC) (Eisert & Pawliszyn, Anal. Chem. 69 (1997) 3140; Chen & Pawliszyn, Anal. Chem. 67 (1995) 2530) SPME is also suitable for other hyphenation, such as supercritical fluid chromatography (Hirata & Pawliszyn, J. Microcol. Sep. 6 (1994) 443), capillary electrophoresis (CE) (Figeys, et al., Nat. Biotechnol. 14 (1996) 1579; Whang, & Pawliszyn, Anal. Commun. 35 (1998) 353), mass spectrometry (MS) (Zhang, & Pawliszyn, Anal. Chem. 65 (1993) 1843), and inductively coupled plasma mass spectrometry (ICP-MS) (Moens, et al., Anal. Chem. 69 (1997) 1604). It is portable and is especially suited for field analysis (Pawliszyn, Sampling and Sample Preparation for Field and Laboratory. Elsevier: New York; (2002)).

However, fiber SPME suffers from unresolved problems, which include fiber breakage, mechanical damage of the coating during operation and handling of the SPME device, and limited sample capacity. These issues led to the development of in-tube SPME (Eisert & Pawliszyn, Anal. Chem. 69 (1997) 3140) also called capillary microextraction (Bigham, et al., Anal. Chem. 74 (2002) 752). In this new format, the sorbent coating is placed on the capillary inner wall. Analytes are extracted by passing the sample through the coated capillary (Lord & Pawliszyn, J. Chromatogr. A 885 (2000) 153). In-tube SPME has a significant advantage over traditional fiber SPME in that the sorbent coating is protected against mechanical damage during operation since it is secured on the inner wall of a capillary. Short segments of GC columns have been used to perform extraction by in-tube SPME (Kataoka &. Pawliszyn, Chromatographia 50 (1999) 532).

Additionally, CME easily couples with HPLC, allowing easier analysis of weakly volatile or thermally labile analytes (Mullett, J. Pawliszyn, J. Sep. Sci. 26 (2003) 251). CME also offers some other advantages over fiber SPME. SPME fibers often have limited sample capacities. Higher sample capacities can be obtained with CME because the sorbent coating bed is contained within a longer segment of the tube providing higher sorbent loading. Fiber SPME devices also have issues with mechanical stability—the fiber can break, the coating can be scratched, and the needle can bend (Djozan, Y. Assadi, S. Haddadi, Anal. Chem. 73 (2001) 4054). CME devices allow for superior mechanical stability because flexible capillaries with outer protective coatings are utilized, providing safeguard against mechanical damage to the sorbent or the tubing.

Conventionally coated GC capillaries for in-tube SPME still limit sample capacity due to diminutive, sub-micrometer thickness of GC coatings, as well as reduced thermal and solvent stability due to a lack of chemical bonds between the coatings and the capillary wall. To address these issues, Malik and co-workers introduced sol-gel capillary microextraction (CME) (Bigham, et al., Anal. Chem. 74 (2002) 752) representing in-tube SPME on fused silica capillaries with surface-bonded sol-gel hybrid organic-inorganic coatings. The use of the capillary format and the covalently bonded sol-gel coating helped overcome the format-related shortcomings of conventional fiber SPME as well as the thermal and solvent stability issues of traditional sorbent coatings.

Ionic liquid (IL)-mediated sol-gel hybrid organic-inorganic materials present enormous potential for effective use in chemical analysis. This opportunity, however, has not yet been explored. One obstacle to materializing this possibility arises from the high viscosity of ILs significantly slowing down sol-gel reactions. This work overcame this hurdle and successfully prepared IL-mediated advanced sol-gel materials for capillary microextraction (CME). In IL-mediated sol-gel processes, ILs are responsible for porous morphology of the created sol-gel materials. However, IL-generated porous morphology alone is not enough to provide effective extraction media; chemical characteristics of both the organic polymer and the precursor play important roles. The present invention teaches how to make proper choices for these ingredients to ensure highly efficient IL-mediated organic-inorganic hybrid extraction media with desired sorbent characteristics.

In recent years, ionic liquids (ILs) (organic salts that melt at or below 100° C.) have gained popularity in a number of fields due to their perceived advantages over traditional solvents. They are considered "green" solvents because they are remarkably less hazardous than their conventional counterparts thanks to negligible vapor pressures, low flammability, good thermal stability, "tunable viscosities," low corrosion tendencies, and varying degrees of solubility with water and organic solvents (S. A. Forsyth, J. M. Pringle, D. R. MacFarlane, Aust. J. Chem. 57 (2004) 113). These properties have led to the use of ILs in a variety of areas including green chemistry (N. V. Plechkova, K. R. Seddon, In Methods and Reagents for Green Chemistry; P. Tundo, A. Perosa, F. Zecchini, Eds.; Wiley: Hoboken, N.J., (2007) 105-130), organic synthesis and catalysis (T. Welton, Chem. Rev. 99 (1999) 2071; R. Sheldon, Chem. Comm. 23 (2001) 2399; C. M. Gordon, Appl. Catal. A 222 (2001) 101; J. Dupont, R. F. de Souza, P. A. Z. Suarez, Chem. Rev. 102 (2002) 3667; D. B. Zhao, M. Wu, Y. Kou, E. Min, Catal. Today 74 (2002) 157), chemical industry (N. V. Plechkova, K. R. Seddon, Chem. Soc. Rev. 37 (2008) 123), electrochemistry (D. R. Macfarlane, M. Forsyth, P. C. Howlett, J. M. Pringle, J. Sun, G. Annat, W. Neil, E. I. Izgorodina, Acc. Chem. Res. 40 (2007) 1165; R. Hagiwara, J. S. Lee, Electrochemistry 75 (2007) 23; D. Wei, A. Ivaska, Anal. Chim. Acta 607 (2008) 126; P. Hapiot, C. Lagrost, Chem. Rev. 108 (2008) 2238), amino acid and peptide chemistry (J. C. Plaquevent, J. Levillain, F. Guillen, C. Malhaic, A. C. Gaumont, Chem. Rev. 18 (2008) 5035), carbohydrate chemistry (O. A. El Seoud, A. Koschella, L. C. Fidale, S. Dorn, T. Heinze, Biomacromolecules 8 (2007) 2629), and in the preparation of microemulsions (Z. M. Qiu, J. Texter, Curr. Opin. Colloid Interface Sci. 13 (2008) 252). Several books and extensive reviews have been also published on ionic liquids and their applications (S. Chowdhury, R. S. Mohan, J. L. Scott, Tetrahedron 63 (2007) 2363; P. Wasserscheid, T. Welton, Ionic Liquids in Synthesis, $2^{nd}$ ed.; Wiley-VCH: Weinheim, Germany (2008); H. Weingartner, Angew. Chem. Int. Ed. 47 (2008) 654).

ILs have also found applications in a number of areas in analytical chemistry, including GC (D. W. Armstrong, L. F. He, Y. S. Liu, Anal. Chem. 71 (1999) 3873; J. L. Anderson, In Ionic Liquids in Chemical Analysis; M. Koel, Ed.; CRC Press: Boca Raton, Fla. (2009) 139-165), LC (L. J. He, W. Z. Zhang, L. Zhao, X. Liu, S. X. Jiang, J. Chromatogr. A 1007 (2003) 39; R. Kaliszan, M. P. Marszall, M. J. Markuszewski, T. Baczek, J. Pernak, J. Chromatogr. A 1030 (2004) 263; M. P. Marszall, R. Kaliszan, Crit. Rev. Anal. Chem. 37 (2007) 127; A. M. Stalcup, In Ionic Liquids in Chemical Analysis; M. Koel, M. Ed.; CRC Press: Boca Raton, Fla. (2009) 168-183), countercurrent chromatography (A. Berthod, S. Carda-Broch, Anal. Bioanal. Chem. 380 (2004) 168), CE (E. G. Yanes, S. R. Gratz, M. J. Baldwin, S. E. Robinson, A. M. Stalcup, Anal. Chem. 73 (2001) 3838; M. Vaher, M. Koel, M. Kaljurand, Electrophoresis 23 (2002) 426; W. D. Qin, S. F. Y. Li, Analyst 128 (2003) 37; M. Lopez-Pastor, B. M. Simonet, B. Lendl, M. Valcarcel, Electrophoresis 29 (2008) 94), analytical spectroscopy (C. D. Tran, Anal. Lett. 40 (2007) 2447), liquid-liquid extractions (J. G. Huddleston, H. D. Willauer, R. P. Swatloski, A. E. Visser, R. D. Rogers, Chem. Comm. 16 (1998) 1765; M. Gharehbaghi, F. Shemirani, M. Baghdadi, Int. J. Environ. Anal. Chem. 89 (2009) 21), solid-phase extraction (G. V. Myasoedova, N. P. Molochnikova, O. B. Mokhodoeva, B. F. Myasoedov, Anal. Sci. 24 (2008) 1351), micro-solvent cluster extraction (T. Charoenraks, M. Tabata, K. Fuji, Anal. Sci. (2008) 1239), SPME (J. F. Liu, N. Li, G. B. Jiang, J. M. Li, J. A. Jonsson, M. J. Wen, J. Chromatogr. A 1066 (2005) 27; Y. N. Hsieh, P. C. Huang, I. W. Sun, T. J. Whang, C. Y. Hsu, H. H. Huang, C. H. Kuei, Anal. Chim. Acta 557 (2006) 321; F. Zhao, Y. Meng, J. L. Anderson, J. Chromatogr. A 1208 (2008) 1), single-drop microextraction (L. Vidal, A. Chisvert, A. Canals, A. Salvador, J. Chromatogr. A 1174 (2007) 95), and supercritical fluid extraction (S. Keskin, D. Kayrak-Talay, U. Akman, O. Hortacsu, J. Supercrit. Fluids 43 (2007) 150). Extensive reviews have been published in on IL applications in the areas of analytical chemistry (S. Pandey, Anal. Chim. Acta 556 (2006) 38; X. Han, D. W. Armstrong, Acc. Chem. Res. 40 (2007) 1079; M. Koel, Ionic Liquids in Chemical Analysis; CRC Press: Boca Raton, Fla.; (2009)).

Recently, ILs have been used in the preparation of sol-gel materials (S. Dai, Y. H. Ju, H. J. Gao, J. S. Lin, S. J. Pennycook, C. E. Barnes, Chem. Commun. 3 (2000) 243; Y. Zhou, J. H. Schattka, M. Antonietti, Nano Lett. 4 (2004) 477; Y. Liu, M. J. Wang, Z. Y. Li, H. T. Liu, P. He, J. H. Li, Langmuir 21 (2005) 1618; Y. Liu, M. J. Wang, J. Li, Z. Y. Li, P. He, H. T. Liu, J. H. Li, Chem. Commun. 13 (2005) 1778; M. A. Klingshirn, S. K. Spear, J. D. Holbrey, R. D. Rogers, J. Mater. Chem. 15 (2005) 5174; H. F. Wang, Y. Z. Zhu, X. P. Yan, R. Y. Gao, J. Y. Zheng, Adv. Mater. 18 (2006) 3266; A. Karout, A. C. Pierre, J. Non-Cryst. Solids 353 (2007) 2900; H. F. Wang, Y. Z. Zhu, J. P. Lin, X. P. Yan, Electrophoresis 29 (2008) 952). In sol-gel applications, ILs have served as solvents (S. Dai, Y. H. Ju, H. J. Gao, J. S. Lin, S. J. Pennycook, C. E. Barnes, Chem. Commun. 3 (2000) 243; Y. Liu, M. J. Wang, Z. Y. Li, H. T. Liu, P. He, J. H. Li, Langmuir 21 (2005) 1618; A. Karout, A. C. Pierre, J. Non-Cryst. Solids 353 (2007) 2900), pore templates (Y. Zhou, J. H. Schattka, M. Antonietti, Nano Lett. 4 (2004) 477; Y. Liu, M. J. Wang, J. Li, Z. Y. Li, P. He, H. T. Liu, J. H. Li, Chem. Commun. 13 (2005) 1778), drying control chemical additives (M. A. Klingshirn, S. K. Spear, J. D. Holbrey, R. D. Rogers, J. Mater. Chem. 15 (2005) 5174), and possibly as a catalyst (A. Karout, A. C. Pierre, J. Non-Cryst. Solids 353 (2007) 2900). In several cases, ILs had significant effects on the porous structure of sol-gel materials (Y. Zhou, J. H. Schattka, M. Antonietti, Nano Lett. 4 (2004) 477; M. A. Klingshirn, S. K. Spear, J. D. Holbrey, R. D. Rogers, J. Mater. Chem. 15 (2005) 5174; A. Karout, A. C. Pierre, J. Non-Cryst. Solids 353 (2007) 2900), reduction in cracking and shrinking (M. A. Klingshirn, S. K. Spear, J. D. Holbrey, R. D. Rogers, J. Mater. Chem. 15 (2005) 5174; H. F. Wang, Y. Z. Zhu, X. P. Yan, R. Y. Gao, J. Y. Zheng, Adv. Mater. 18 (2006) 3266; A. Safavi, N. Maleki, M. Bagheri, J. Mater. Chem. 17 (2007) 1674) during solvent evaporation from the sol-gel pores, and sol-gel reaction kinetics (M. A. Klingshirn, S. K. Spear, J. D. Holbrey, R. D. Rogers, J. Mater. Chem. 15

(2005) 5174; A. Karout, A. C. Pierre, J. Non-Cryst. Solids 353 (2007) 2900; K. S. Yoo, T. G. Lee, J. Kim, Microp. Mesopr. Mater. 84 (2005) 211; H. Choi, Y. J. Kim, R. S. Varma, D. D. Dionysiou, Chem. Mater. 18 (2006) 5377).

Ionic liquid-mediated sol-gels have only seldom been used in analytical separations. Yan and co-workers utilized IL-mediated sol-gel monoliths in CEC (H. F. Wang, Y. Z. Zhu, X. P. Yan, R. Y. Gao, J. Y. Zheng, Adv. Mater. 18 (2006) 3266; H. F. Wang, Y. Z. Zhu, J. P. Lin, X. P. Yan, Electrophoresis 29 (2008) 952) for the separation of chiral molecules. Racemic mixtures of naproxen (H. F. Wang, Y. Z. Zhu, X. P. Yan, R. Y. Gao, J. Y. Zheng, Adv. Mater. 18 (2006) 3266) and zolmitriptan (H. F. Wang, Y. Z. Zhu, J. P. Lin, X. P. Yan, Electrophoresis 29 (2008) 952) were analyzed using the IL-mediated sol-gel monoliths. In these cases, 1-butyl-3-methylimmidazolium tetrafluoroborate IL was used to assist in a non-hydrolytic sol-gel process to prepare molecularly imprinted silica-based monoliths. The IL might have helped mitigate the sol-gel shrinking problem and acted as a template for pores (H. F. Wang, Y. Z. Zhu, X. P. Yan, R. Y. Gao, J. Y. Zheng, Adv. Mater. 18 (2006) 3266).

Polar sol-gel sorbents have been developed for in-tube SPME including those based on cyano (Kulkarni, et al., J. Chromatogr. A 1124 (2006) 205), crown ether (Zeng, et al., Anal. Chem. 73 (2001) 2429), and poly(ethylene glycol) (Bigham, et al., Anal. Chem. 74 (2002) 75; Wang, et al., J. Chromatogr. A 893 (2000) 157; Silva & Augusto, J. Chromatogr. A 1072 (2005) 7; Bagheri, et al., J. Chromatogr. B 818 (2005) 147; Kulkarni, et al., J. Chromatogr. A 1174 (2007) 50) materials. While these sol-gel coatings have advanced the use of polar organic polymers and achieve higher thermal and solvent stability, these coatings mostly contain long-chain polymers of high molecular weights (Bigham, et al., Anal. Chem. 74 (2002) 75; Wang, et al., J. Chromatogr. A 893 (2000) 157; Silva & Augusto, J. Chromatogr. A 1072 (2005) 7; Bagheri, et al., J. Chromatogr. B 818 (2005) 147) having lower polarity (compared to their short-chain counterparts), and thus, reduced ability to extract highly polar analytes. For such capillaries, sample capacity can still be an issue (Bagheri, et al., J. Chromatogr. B 818 (2005) 147). However, what is needed is a method of developing a matrix having improved analyte absorbance qualities

SUMMARY OF INVENTION

A sol-gel coatings were prepared using ionic liquids. The coating uses a first sol-gel precursor, such as PDMS, BMPO, polyTHF, PEG, or PDMDPS. An ionic liquid, such as a phosphonium-based ionic liquid, imidazolium-based ionic liquid, pyridinium-based ionic liquid, or a combination thereof, is added to the sol-gel precursor, and mixed with a second sol-gel precursor into the precursor mixture, where the second sol-gel precursor is an alkoxysilane. A catalyst is added, such as an acid, base, or fluoride compound, to begin hydrolysis and or polymerization. In particular examples, the catalyst is an organic acid, such as an acid having a pKa of less than 4. Alternatively, the catalyst can be TFA.

The first sol-gel precursor can be any alkoxysilane sol-gel precursor. In particular, any known alkoxysilane may be used, though longer polymer chains lower the rate of hydrolysis and increase the time required to form a sol-gel. Non-limiting examples of sol-gel precursors include tetramethoxyl silane, or tetraethyl orthosilicate, triethoxysilane, trimethoxysilane, N-(2-aminoethyl)-3-aminopropyltrimethoxysilane, 3-methacryloxypropyltrimethoxysilane, N-[2(vinylbenzylamino)-ethyl]-3-aminopropyltrimethoxysilane, of 3-glycidoxypropyltrimethoxysilane, tetraethoxysilane, methyltrimethoxysilane, methyltriethoxysilane, dimethyldimethoxysilane, dimethyldiethoxysilane, methyldimethoxysilane, methyldiethoxysilane, phenyltrimethoxysilane, trimethylmethoxysilane, trimethylethoxysilane, dimethylmethoxysilane, dimethylethoxysilane, phenyltriethoxysilane, diphenyldimethoxysilane, diphenyldiethoxysilane, phenyldimethoxysilane, phenyldiethoxysilane, phenylmethyldimethoxysilane, phenylmethyldiethoxysilane, triphenylmethoxysilane, triphenylethoxysilane, phenyldimehtylmethoxysilane, phenyldimehtylethoxysilane, diphenylmethylmethoxysilane, diphenylmethylethoxysilane, diphenylmethoxysilane, diphenylethoxysilane, bis(trimethoxysilyl)methane, bis(triethoxysilyl)methane, 1,2-bis(trimethoxysilyl)ethane, 1,2-bis(triethoxysilyl)ethane, 1,4-bis(trimethoxysilyl)benzene, and 1,4-bis(triethoxysilyl)benzene.

A solvent is optionally added to ensure the solubility and appropriate phase of the sol-gel components, as a homogeneous system. The use of the solvent is dictated by the sol-gel components, and are within the skill of one in the art to select the appropriate solvent. Non-limiting examples include methylene chloride, methanol, ethanol, tetrahydrofuran, and mixtures thereof.

The ionic liquids allow for the introduction of pores in the sol-gel matrix. The ionic liquids possess sol-gel active sites, such as hydroxyl- or alkoxy-functional groups, or functional groups that may be converted into a hydroxyl- or alkoxy-functional group, such as the methoxy group of BMPO. Examples of ionic liquids include phosphonium-based ionic liquids, methylimidazolium-based ionic, imidazolium-based ionic liquids, and pyridinium-based ionic liquids (Wasserscheid & Keim, Angew. Chem. Int. Ed. Engl. 2000, 39, 3772). Specific variations of the invention may use TTPT, MOIC, or BMPT. However, other ionic liquids are contemplated and can be substituted.

Exemplary phosphonium-based ionic liquids include trihexyl(2-hydroxyethyl)phosphonium octylsulfate; [4-(Acetyloxy)butyl]trihexylphosphonium iodide; [2-(Heptyloxy)-2-oxoethyl]trihexylphosphonium bromide; Trihexyl(2-oxo-2-propoxyethyl)phosphonium bromide; Trihexyl[2-oxo-2-(pentyloxy)ethyl]phosphonium bromide; [4-(Acetyloxy) butyl]tricyclohexylphosphonium octylsulfate; [4-(Acetyloxy)butyl]tricyclohexylphosphonium 1,1,1-trifluoro-N-[(trifluoromethyl)sulfonyl]methanesulfonamide; [4-(Acetyloxy)butyl]tricyclohexylphosphonium iodide; Tricyclohexyl[2-(heptyloxy)-2-oxoethyl]phosphonium octylsulfate; Tricyclohexyl[2-(heptyloxy)-2-oxoethyl]phosphonium 1,1,1-trifluoro-N-[(trifluoromethyl)sulfonyl] methanesulfonamide; Tricyclohexyl[2-(heptyloxy)-2-oxoethyl]phosphonium bromide; Tricyclohexyl[2-oxo-2-(pentyloxy)ethyl]phosphonium octylsulfate; Tricyclohexyl [2-oxo-2-(pentyloxy)ethyl]phosphonium 1,1,1-trifluoro-N-[(trifluoromethyl)sulfonyl]methanesulfonamide; Trihexyl(2-propen-1-yl)phosphonium bromide; Trihexyl (methoxymethyl)phosphonium chloride; Trihexyl(2-hydroxyethyl)phosphonium bromide; Trihexyl (methoxymethyl)phosphonium octylsulfate; Trihexyl(2-propen-1-yl)phosphonium octylsulfate; [4-(Acetyloxy) butyl]trihexylphosphonium octylsulfate;[2-(Heptyloxy)-2-oxoethyl]trihexylphosphonium octylsulfate; Trihexyl[2-oxo-2-(pentyloxy)ethyl]phosphonium octylsulfate; Trihexyl(2-oxo-2-propoxyethyl)phosphonium octylsulfate; Trihexyl (methoxymethyl)phosphonium 1,1,1-trifluoro-N-[(trifluoromethyl)sulfonyl]methanesulfonamide; Trihexyl(2-propen-1-yl)phosphonium 1,1,1-trifluoro-N-[(trifluoromethyl)sulfonyl]methanesulfonamide; [4-(Acetyloxy)butyl]trihexylphosphonium 1,1,1-trifluoro-N-[(trifluoromethyl)sulfonyl] methanesulfonamide; [2-(Heptyloxy)-2-oxoethyl]trihexylphosphonium 1,1,1-trifluoro-N-[(trifluoromethyl) sulfonyl]methanesulfonamide; Trihexyl[2-oxo-2-(pentyloxy)ethyl]phosphonium 1,1,1-trifluoro-N-[(trifluoromethyl)sulfonyl]methanesulfonamide; Trihexyl(2-oxo-2-propoxyethyl)phosphonium 1,1,1-trifluoro-N-[(trifluoromethyl)sulfonyl]methanesulfonamide; Tricyclohexyl[2-oxo-2-(pentyloxy)ethyl]phosphonium bromide; Tricyclohexyl(2-oxo-2-propoxyethyl)phosphonium octylsulfate; Trihexyltetradecylphosphonium "dodecylbenzenesulfonate"; Tributyltetradecylphosphonium "dodecylbenzenesulfonate"; Trihexyl (2-hydroxyethyl)phosphonium 1,1,1-trifluoro-N-[(trifluoromethyl)sulfonyl]methanesulfonamide; Trihexyltetradecylphosphonium trifluoromethanesulfonate; Ethyltrihexylphosphonium bromide; Trihexylpropylphosphonium bromide; Butyltrihexylphosphonium bromide; Tetrahexylphosphonium chloride; Heptyltrihexylphosphonium chloride; Tricyclohexyl(2-oxo-2-propoxyethyl)phosphonium 1,1,1-trifluoro-N-[(trifluoromethyl)sulfonyl]methanesulfonamide; Tricyclohexyl(2-oxo-2-propoxyethyl)phosphonium bromide; Tetrahexylphosphonium bromide; Trihexyltetradecylphosphonium methanesulfonate; Hexadecyltrihexylphosphonium chloride; Dodecyltrihexylphosphonium chloride; Decyltrihexylphosphonium chloride; Trihexyloctylphosphonium chloride; Trihexyltetradecylphosphonium trifluorotris(pentafluorethyl)phosphate(1-); Trihexyltetradecylphosphonium tetrafluoroborate(1-); Trihexyltetradecylphosphonium N-cyanocyanamide; Trihexyltetradecylphosphonium decanoate; Trihexyltetradecylphosphonium bis(2,4,4-trimethylpentyl)phosphinate; Trihexyltetradecylphosphonium 1,1,1-trifluoro-N-[(trifluoromethyl)sulfonyl]methanesulfonamide; Methyltris(2-methylpropyl)phosphonium 4-methylbenzenesulfonate; Tetrabutylphosphonium bis[1,2-benzenediolato(2-)-$O_1,O_2$]borate(1-); Trihexyltetradecylphosphonium hexafluorophosphate(1-); Trihexyltetradecylphosphonium bromide; Tetrabutylphosphonium bromide; and Tributylethylphosphonium diethyl phosphate.

Exemplary imidazolium-based ionic liquids include 1-Methyl-3-propyl-1H-imidazolium bromide; 1-Methyl-3-(2-oxo-2-propoxyethyl)-1H-imidazolium octylsulfate; 1-(2-Hydroxyethyl)-3-methylimidazolium tetrafluoroborate; 1,3-Didecyl-2-methyl-1H-imidazolium 1,1,1-trifluoro-N-[(trifluoromethyl)sulfonyl]methanesulfonamide; 1H-Imidazolium, 1-ethyl-2-(8-heptadecenyl)-4,5-dihydro-3-(2-hydroxyethyl)-, ethyl sulfate; Imidazolium compounds, 2-(C17 and C17-unsatd. alkyl)-1-[2-(C18 and C18-unsatd. amido)ethyl]-4,5-dihydro-1-methyl, Mesulfates; 1-Ethyl-3-methyl-1H-imidazolium acetate; 1-Methyl-3-(3,3,4,4,5,5,6,6,7,7,8,8,8-tridecafluorooctyl)-1H-imidazolium hexafluorophosphate(1-); 1-Methyl-3-[2-oxo-2-(pentyloxy)ethyl]-1H-imidazolium bromide; 1-Butyl-3-methyl-1H-imidazolium thiocyanate; 1-(7-Carboxyheptyl)-3-methyl-1H-imidazolium bromide; 1-(8-Hydroxyoctyl)-1-methyl-1H-imidazolium bromide; 1-Methyl-3-(3-oxobutyl)-1H-imidazolium bromide; 3-(3-Carboxypropyl)-1-methyl-1H-imidazolium chloride; 1-(4-Hydroxybutyl)-3-methyl-1H-imidazolium chloride; 1-Methyl-3-(2-propenyl)-1H-imidazolium chloride; 1-Butyl-3-methyl-1H-imidazolium 2-(2-methoxyethoxy)ethyl sulfate; 1-Methyl-3-(2-phenylethyl)-1H-imidazolium tetrafluoroborate(1-); 1-Methyl-3-(2-oxo-2-propoxyethyl)-1H-imidazolium bromide; 1-Methyl-3-[2-oxo-2-(pentyloxy)ethyl]-1H-imidazolium octylsulfate; 1-Methyl-3-(2-oxo-2-propoxyethyl)-1H-imidazolium 1,1,1-trifluoro-N-[(trifluoromethyl)sulfonyl]methanesulfonamide; 1-Methyl-3-(2-oxo-2-propoxyethyl)-1H-imidazolium N-cyanocyanamide; 1-Methyl-3-(2-oxo-2-propoxyethyl)-1H-imidazolium hexafluorophosphate(1-); 1-Methyl-3-(2-oxo-2-propoxyethyl)-1H-imidazolium tetrafluoroborate(1-); 1-Methyl-3-[2-(octyloxy)-2-oxoethyl]-1H-imidazolium bromide; 3-[2-(Hexyloxy)-2-oxo ethyl]-1-methyl-1H-imidazolium bromide; 3-(2-Butoxy-2-oxoethyl)-1-methyl-1H-imidazolium bromide; 3-(2-Methoxy-2-oxoethyl)-1-methyl-1H-imidazolium bromide; 3-[2-(Diethylamino)-2-oxo ethyl]-1-methyl-1H-imidazolium bromide; 3-[2-(Butylmethylamino)-2-oxo ethyl]-1-methyl-1H-imidazolium bromide; 3-[2-(Butylamino)-2-oxo ethyl]-1-methyl-1H-imidazolium bromide; 3-(2-Ethoxy-2-oxoethyl)-1-methyl-1H-imidazolium tetrafluoroborate(1-); 3-(2-Ethoxy-2-oxoethyl)-1-methyl-1H-imidazolium bromide; 1,2-Dimethyl-3-[2-oxo-2-(pentyloxy)ethyl]-1H-imidazolium bromide; 1,2-Dimethyl-3-[2-oxo-2-(pentyloxy)ethyl]-1H-imidazolium octylsulfate; 1,2-Dimethyl-3-(2-oxo-2-propoxyethyl)-1H-imidazolium bromide; 1,2-Dimethyl-3-(2-oxo-2-propoxyethyl)-1H-imidazolium octylsulfate; 1-Methyl-3-(2-phenylethyl)-1H-imidazolium hexafluorophosphate(1-); 1-Methyl-3-(2-phenylethyl)-1H-imidazolium chloride; 1-Methyl-3-(phenylmethyl)-1H-imidazolium tetrafluoroborate(1-); 1-Ethyl-3-propyl-1H-imidazolium bromide; 1-Methyl-3-nonyl-1H-imidazolium tetrafluoroborate(1-); 1-Ethyl-3-hexyl-1H-imidazolium bromide; 1-Ethyl-3-hexyl-1H-imidazolium tetrafluoroborate(1-); 1-Heptyl-3-methyl-1H-imidazolium hexafluorophosphate(1-); 1-Heptyl-3-methyl-1H-imidazolium tetrafluoroborate(1-); 1,3-Diethyl-1H-imidazolium bromide; 1-Methyl-3-nonyl-1H-imidazolium hexafluorophosphate(1-); 1-Decyl-3-ethyl-1H-imidazolium bromide; 1-Methyl-3-pentyl-1H-imidazolium tetrafluoroborate(1-); 1-Methyl-3-[(4-methylphenyl)methyl]-1H-imidazolium chloride; 1-Methyl-3-pentyl-1H-imidazolium hexafluorophosphate(1-); 1-Methyl-3-[(4-methylphenyl)methyl]-1H-imidazolium hexafluorophosphate(1-); 1-Methyl-3-propyl-1H-imidazolium hexafluorophosphate(1-); 1-Ethyl-3-methyl-1H-imidazolium trifluorotris(pentafluoroethyl)phosphate(1-); 1-Ethyl-3-methyl-1H-imidazolium bis[ethanedioato(2-)-$O_1,O_2$]borate(1-); 1-Ethyl-3-methyl-1H-imidazolium bis[1,2-benzenediolato(2-)-$O_1,O_2$]borate(1-); 1-Butyl-3-methyl-1H-imidazolium N-cyanocyanamide; 1-Butyl-2,3-dimethyl-1H-imidazolium tetrafluoroborate(1-); 1-Hexyl-2,3-dimethyl-1H-imidazolium tetrafluoroborate(1-); 1-Ethyl-3-methyl-1H-imidazolium bis(pentafluoroethyl)phosphinate; 1-Decyl-3-methyl-1H-imidazolium bromide; 1-Butyl-3-methyl-1H-imidazolium trifluoromethanesulfonate; 1-Hexyl-3-methyl-1H-imidazolium 1,1,1-trifluoro-[(trifluoromethyl)sulfonyl]methanesulfonamide; 1-Decyl-3-methyl-1H-imidazolium chloride; 1-Methyl-3-tetradecyl-1H-imidazolium chloride; 1-Ethyl-3-methyl-1H-imidazolium chloride; 1-Butyl-3-methyl-1H-imidazolium hexafluorophosphate(1-); 1-Butyl-3-methyl-1H-imidazolium tetrafluoroborate(1-); 1-Hexyl-3-methyl-1H-imidazolium chloride; 1-Ethyl-3-methyl-1H-imidazolium tetrafluoroborate(1-); 1-Methyl-3-octyl-1H-imidazolium hexafluorophosphate(1-); 1-Ethyl-3-methyl-1H-imidazolium trifluoromethanesulfonate; 1-Ethyl-3-methyl-1H-imidazolium hexafluorophosphate(1-); 1-Methyl-3-octyl-1H-imidazolium chloride; 1-Butyl-3-methyl-1H-imidazolium methyl sulfate; 1-Hexyl-3-methyl-1H-imidazolium tetrafluoroborate(1-); 1-Hexyl-3-methyl-1H-imidazolium hexafluorophosphate(1-); 1-Methyl-3-octyl-1H-imidazolium tetrafluoroborate(1-); 1-Hexyl-3-methyl-1H-imidazolium trifluorotris(pentafluoroethyl)phosphate(1-); 1-Butyl-3-methyl-1H-imidazolium chloride; 1-Hexadecyl-3-methyl-1H-imidazolium chloride; 1-Butyl-3-methyl-1H-imidazolium bromide; 1-Butyl-3-methyl-1H-imidazolium 1,1,1-trifluoro-N-(trifluoromethyl)methanaminate; 1-Butyl-3-methyl-1H-imidazolium (OC-6-11)- hexafluoroantimonate(1-); 1-Butyl-3-methyl-1H-imidazolium 1,1,1-trifluoro-N-[(trifluoromethyl)sulfonyl]methanesulfonamide; 1-Methyl-3-octadecyl-1H-imidazolium chloride; 1-Methyl-3-octyl-1H-imidazolium 1,1,1-trifluoro-N-[(trifluoromethyl)sulfonyl]methanesulfonamide; 1-Butyl-3-methyl-1H-imidazolium 4-methylbenzenesulfonate; 1-Butyl-3-methyl-1H-imidazolium (T-4)-tetracarbonylcobaltate (1-); 1-Butyl-2,3-dimethyl-1H-imidazolium trifluoromethanesulfonate; 1-Methyl-3-(phenylmethyl)-1H-imidazolium hexafluorophosphate(1-); 1-Ethyl-3-methyl-1H-imidazolium trifluoroacetate; 1-Ethyl-3-methyl-1H-imidazolium N-cyanocyanamide; 1-Methyl-3-(phenylmethyl)-1H-imidazolium chloride; 1-Ethyl-3-methyl-1H-imidazolium methyl sulfate; 1-Ethyl-3-methyl-1H-imidazolium 4-methylbenzenesulfonate; 1-Butyl-3-methyl-1H-imidazolium octylsulfate; 3-Methyl-1-octyl-1H-imidazolium octylsulfate; 1-Butyl-3-methyl-1H-imidazolium iodide; 1-Ethyl-3-methyl-1H-imidazolium 1,1,1-trifluoro-N-[(trifluoromethyl)sulfonyl]methanesulfonamide; 1-Ethyl-3-methyl-1H-imidazolium thiocyanate; 1-Methyl-3-propyl-1H-imidazolium iodide; 1-Ethyl-3-methyl-1H-imidazolium octylsulfate; 1-Ethyl-3-methyl-1H-imidazolium hydrogen sulfate; 1-Ethyl-3-methyl-1H-imidazolium ethyl sulfate; 1-Butyl-3-methyl-1H-imidazolium hydrogen sulfate; 1-Ethyl-3-methyl-1H-imidazolium tetracyanoborate(1-); 1-Butyl-3-methyl-1H-imidazolium trifluorotris(pentafluoroethyl)phosphate(1-); 1-(Cyanomethyl)-3-methyl-1H-imidazolium 1,1,1-trifluoro-N-[(trifluoromethyl)sulfonyl]methanesulfonamide; 1-(2-Hydroxyethyl)-3-methyl-1H-imidazolium 1,1,1-trifluoro-N-[(trifluoromethyl)sulfonyl]methanesulfonamide; 1-Methyl-3-octyl-1H-imidazolium bromide; 1-Ethyl-3-methyl-1H-imidazolium methanesulfonate; 1-Butyl-3-methyl-1H-imidazolium methanesulfonate; 1-Ethyl-3-methyl-1H-imidazolium 2-(2-methoxyethoxy)ethyl sulfate; 1-Methyl-3-(phenylmethyl)-1H-imidazolium tetrafluoroborate(1-); 1-Hexyl-3-methyl-1H-imidazolium bromide; 1-Hexyl-3-methyl-1H-imidazolium trifluorotris(heptafluoropropyl)phosphate(1-); 1-Methyl-3-octylimidazolium trifluormethanesulfonate; 1-Methyl-3-pentyl-1H-imidazolium chloride; 1-Heptyl-3-methyl-1H-imidazolium chloride; 1-Decyl-3-methyl-1H-imidazolium tetrafluoroborate(1-); 1-Methyl-3-nonyl-1H-imidazolium chloride; 1-Decyl-3-methyl-1H-imidazolium hexafluorophosphate(1-); 1-Methyl-3-propyl-1H-imidazolium chloride; 1-(2-Ethoxyethyl)-3-methyl-1H-imidazolium bromide; 1-(2-Ethoxyethyl)-3-methyl-1H-imidazolium 1,1,1-trifluoro-N-[(trifluoromethyl)sulfonyl]methanesulfonamide; 1-(2-Methoxyethyl)-3-methyl-1H-imidazolium 1,1,1-trifluoro-N-[(trifluoromethyl)sulfonyl]methanesulfonamide; 1-(2-Hydroxyethyl)-3-methyl-1H-imidazolium iodide; 1-(3-Methoxypropyl)-3-methyl-1H-imidazolium 1,1,1-trifluoro-N; [(trifluoromethyl)sulfonyl]methanesulfonamide; 1-(Ethoxymethyl)-3-methyl-1H-imidazolium 1,1,1-trifluoro-N [(trifluoromethyl)sulfonyl]methanesulfonamide; 1-Hexyl-3-methyl-1H-imidazolium tris[(trifluoromethyl)sulfonyl]methide (1:1); 1-Methyl-3-propyl-1H-imidazolium tetrafluoroborate(1-); 1-(3-Methoxypropyl)-3-methyl-1H-imidazolium chloride; 1-(2-Methoxyethyl)-3-methyl-1H-imidazolium chloride; 1-(Cyanomethyl)-3-methyl-1H-imidazolium chloride; 1-(3-Hydroxypropyl)-3-methyl-1H-imidazolium 1,1,1-trifluoro-N-[(trifluoromethyl)sulfonyl]methanesulfonamide; 1-Octyl-3-methyl-1H-imidazolium trifluorotris(pentafluoroethyl)phosphate(1-); 1-Butyl-3-methyl-1H-imidazolium tetrachloroferrate(1-); 1-Butyl-3-ethyl-1H-imidazolium trifluoromethanesulfonate; 1-Butyl-3-ethyl-1H-imidazolium trifluoroacetate; 1-Hexyl-3-methyl-1H-imidazolium, salt with 1,2-benzisothiazol-3(2H)-one 1,1-dioxide (1:1); 1-(Ethoxymethyl)-3-methyl-1H-imidazolium chloride; 1-(3-Hydroxypropyl)-3-methyl-1H-imidazolium chloride; 1-Butyl-3-ethyl-1H-imidazolium tetrafluoroborate(1-); 3-alkoxymethyl-1-methylimidazolium salts of Cl$^-$, BF$_4^-$ and PF$_6^-$; 1-ethyl-3-methylimidazolium dicyanamide; 1-butyl-3-methylimidazolium nitratel-alkyl-3-methylimidazolium; 1-alkylpyridiniuml-butyl-3-methylimidazolium tetrafluoroborate; and 1-butyl-3-methylimidazolium chloride Exemplary pyridinium-based ionic liquids include 1-(Butoxymethyl)-3-hydroxypyridinium 6-methyl-2,2-dioxo-1,2,3-oxathiazin-4(3H)-onate (1:1); 3-Methyl-1-octylpyridinium bromide; 1-[(Heptyloxy)methyl]-3-hydroxypyridinium, salt with 1,2-benzisothiazol-3(2H)-one 1,1-dioxide (1:1); 1-[(Heptyloxy)methyl]-3-hydroxypyridinium chloride; 3-Hydroxy-1-(propoxymethyl)pyridinium chloride; 3-Hydroxy-1-(propoxymethyl)pyridinium, salt with 1,2-benzisothiazol-3(2H)-one 1,1-dioxide (1:1); 3-Hydroxy-1-(propoxymethyl)pyridinium 6-methyl-2,2-dioxo-1,2,3-oxathiazin-4(3H)-onate (1:1); 1-Butyl-3,5-dimethylpyridinium bromide; 3-(Butoxycarbonyl)-1-butylpyridinium octyl sulfate; 3-(Butoxycarbonyl)-1-methylpyridinium 1,1,1-trifluoro-N-[(trifluoromethyl)sulfonyl]methanesulfonamide(1-); 3-(Butoxycarbonyl)-1-methylpyridinium iodide; 3-(Butoxycarbonyl)-1-methylpyridinium octyl sulfate; 1-(2-Ethoxy-2-oxoethyl)pyridinium octyl sulfate; 3-Hydroxy-1-[(undecyloxy)methyl]pyridinium, salt with 1,2-benzisothiazol-3(2H)-one 1,1-dioxide (1:1); 1-Butylpyridinium N-cyano cyanamide; 3-Hydroxy-1-[(undecyloxy)methyl]pyridinium 6-methyl-2,2-dioxo-1,2,3-oxathiazin-4(3H)-onate (1:1); 1-Butyl-3,5-dimethylpyridinium N-cyano cyanamide; 3-Methyl-1-propylpyridinium bromide; 3-Hydroxy-1-[(octadecyloxy)methyl]pyridinium, salt with 1,2-benzisothiazol-3(2H)-one 1,1-dioxide (1:1); 1-Butyl-3-[(butylamino)carbonyl]pyridinium octyl sulfate; 3-Hydroxy-1-[(octadecyloxy)methyl]pyridinium 6-methyl-2,2-dioxo-1,2,3-oxathiazin-4(3H)-onate (1:1); 1-[(Hexyloxy)methyl]-3-hydroxypyridinium 6-methyl-2,2-dioxo-1,2,3-oxathiazin-4(3H)-onate (1:1); 1-[(Hexyloxy)methyl]-3-hydroxypyridinium, salt with 1,2-benzisothiazol-3(2H)-one 1,1-dioxide (1:1); 1-(Butoxymethyl)-3-hydroxypyridinium, salt with 1,2-benzisothiazol-3(2H)-one 1,1-dioxide (1:1); 1-Hexyl-3-methylpyridinium bromide; 1-[(Heptyloxy)methyl]-3-hydroxypyridinium 6-methyl-2,2-dioxo-1,2,3-oxathiazin-4(3H)-onate (1:1); 3-Hydroxy-1-[(undecyloxy)methyl]pyridinium chloride; 1-(2-Ethoxy-2-oxo ethyl)pyridinium bromide; 1-Butyl-3,4-dimethylpyridinium chloride; 1-Butylpyridinium chloride; 1-Butylpyridinium tetrafluoroborate(1-); 1-Butylpyridinium hexafluorophosphate(1-); 1-Butyl-4-methylpyridinium chloride; 1-Butyl-4-methylpyridinium tetrafluoroborate(1-); 1-Butyl-4-methylpyridinium hexafluorophosphate(1-); 1-Hexylpyridinium hexafluorophosphate (1-); 1-Butyl-3-methylpyridinium bromide; 4-Methyl-1-octylpyridinium chloride; 1-Butylpyridinium methyl sulfate; 1-Butylpyridinium bromide; 1-Butyl-3,5-dimethylpyridinium chloride; 1-Butyl-3-methylpyridinium chloride; 1-Butyl-3-methylpyridinium tetrafluoroborate(1-); 1-Hexylpyridinium 1,1,1-trifluoro-N-[(trifluoromethyl)sulfonyl]methanesulfonamide; 1-Butylpyridinium trifluoromethanesulfonate; 1-Hexylpyridinium trifluoromethanesulfonate; 1-Octylpyridinium 1,1,1-trifluoro-N-[(trifluoromethyl)sulfonyl]methanesulfonamide; 1-Octylpyridinium chloride; 1-Ethylpyridinium chloride; 1-Butyl-3-methylpyridinium hexafluorophosphate (1-); 4-(Dimethylamino)-1-hexylpyridinium 1,1,1-trifluoro-N-[(trifluoromethyl)sulfonyl]methanesulfonamide; 1-(3-Hydroxypropyl)pyridinium 1,1,1-trifluoro-N-[(trifluoromethyl)sulfonyl]methanesulfonamide; 1-Butyl-3-methylpyridinium N-cyanocyanamide; 1-Hexyl-3-methylpyridinium chloride; 1-Hexyl-4-methylpyridinium chloride; 3-Methyl-1-octylpyridinium chloride; 1-Hexylpyridinium chloride; 1-(2-Methoxyethyl)pyridinium chloride; 1-(3-Hydroxypropyl)pyridinium chloride; 1-(2-Ethoxyethyl)pyridinium 1,1,1-trifluoro-N-[(trifluoromethyl)sulfonyl]methanesulfonamide; 1-(2-Ethoxyethyl)pyridinium bromide; 1-(Ethoxymethyl)pyridinium chloride; 1-(2-Hydroxyethyl)pyridinium iodide; 4-Methyl-1-octylpyridinium tetrafluoroborate (1-); 1-Hexyl-4-methylpyridinium tetrafluoroborate (1-); 1-Butyl-2-methylpyridinium tetrafluoroborate(1-); 1-Butyl-3,4-dimethylpyridinium tetrafluoroborate(1-); 1-Butyl-3,5-dimethylpyridinium tetrafluoroborate(1-); 4-(Dimethylamino)-1-ethylpyridinium 1,1,1-trifluoro-N-[(trifluoromethyl)sulfonyl]methanesulfonamide; 1-(Ethoxymethyl)pyridinium 1,1,1-trifluoro-N-[(trifluoromethyl)sulfonyl]methanesulfonamide; 1-(2-Methoxyethyl)pyridinium 1,1,1-trifluoro-N-[(trifluoromethyl)sulfonyl]methanesulfonamide; 1-Butyl-4-(dimethylamino)pyridinium 1,1,1-trifluoro-N-[(trifluoromethyl) sulfonyl] methanesulfonamide; 1-(2-Hydroxyethyl)pyridinium 1,1,1-trifluoro-N-[(trifluoromethyl)sulfonyl]methanesulfonamide; 4-(Dimethylamino)-1-hexylpyridinium chloride; 1-Butyl-2-methylpyridinium chloride; 1-Butyl-4-(dimethylamino)pyridinium chloride; 1-Propylpyridinium bromide; 1-Propylpyridinium 1,1,1-trifluoro-N-[(trifluoromethyl)sulfonyl]methanesulfonamide; 1-Pentylpyridinium bromide; 1-Pentylpyridinium 1,1,1-trifluoro-N-[(trifluoromethyl)sulfonyl]methanesulfonamide; 1-Butyl-4-methylpyridinium tetracyanoborate(1-); 4-(Dimethylamino)-1-ethylpyridinium bromide; 1-Butyl-4-methylpyridinium trifluorotris(pentafluoroethyl)phosphate(1-); 1-(3-Sulfopropyl)pyridinium trifluoromethanesulfonate; 1-(3-Methoxypropyl)pyridinium 1,1,1-trifluoro-N-[(trifluoromethyl)sulfonyl]methanesulfonamide; 4-(Dimethylamino)-1-methylpyridinium iodide; 1-(3-Methoxypropyl)pyridinium chloride; 1-(Cyanomethyl)pyridinium chloride; 1-(Cyanomethyl)pyridinium 1,1,1-trifluoro-N-[(trifluoromethyl)sulfonyl]methanesulfonamide; 1-Butylpyridinium μ-chlorohexachlorodialuminate; N-ethylpyridinium tetrafluoroborate; N-ethylpyridinium trifluoroacetate; 1-butyl-3-methylimidazolium hexafluorophosphate; 1-alkyl-3-methylimidazolium; pyridinium chloride; 1-butyl-3,5-dimethylpyridinium bromide; N-methyl-N-alkylpyrrolidinium; 1-ethylpyridinium chloride, and 1-butyl-3-methylimidazolium chloride.

The disclosed mixture may be coated to the inner wall of an extraction column, such as a extraction column or capillary. For example, the sol-gel mixture may be added to the interior lumen of an extraction column and allowed to bond to the interior wall of the extraction column. Following bonding, any unbonded sol-gel mixture is removed from the extraction column. After coating, the column is optionally conditioned in a gas chromatography oven by elevating the temperature of the gas chromatography oven at until the oven reaches a conditioning temperature. The conditioning temperature varies based on the sol-gel and ionic liquid constituents, but is generally between about 110° C. and 300° C. For example, the conditioning may be at 120° C., 230° C., 240° C., 150° C., 160° C., 170° C., 180° C., 190° C., 200° C., 220° C., 240° C., 250° C., 260° C., 280° C., or 300° C.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
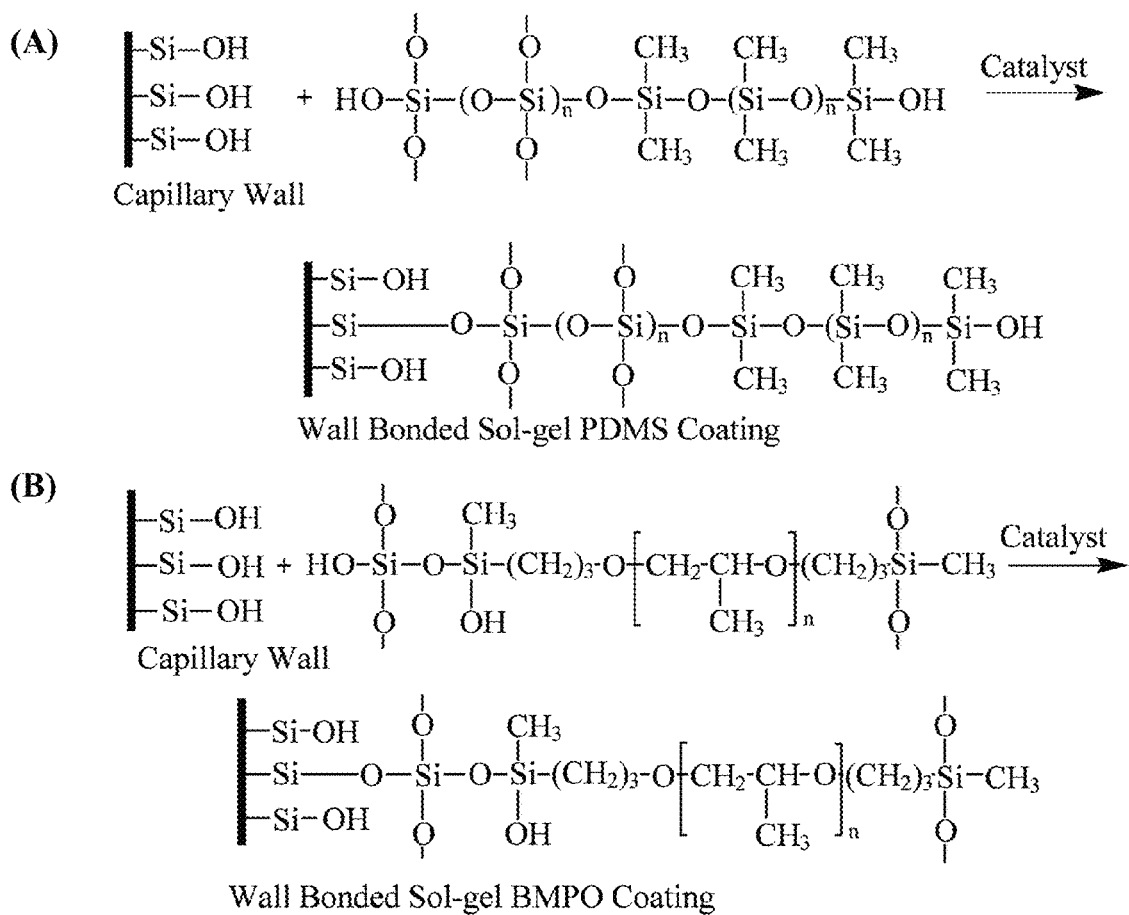
FIGS. 1(A) and (B) are reaction schemes depicting the polycondensation of 3D sol-gel network to fused silica capillary wall for (A) PDMS and (B) BMPO.

The disclosures below are illustrative only. The amounts and or ratios of components will vary based on the sol-gel precursor and ionic liquid selected. Additionally, the use of catalyst will affect the rate of hydrolysis and may also allow variation from the ratios disclosed.

As used herein, "ionic liquid" means a salt comprising a cation and an anion. The salt (or hydrate or solvate of the sale) is a liquid at ambient or near ambient temperature, specifically having a melting point or range less than about 100° C., and possesses broad solvating properties for a range of polar and non-polar compounds. An ionic liquid may comprise different salts, such as mixtures of salts comprising two or more different cations, anions, or both. Hydrates and solvates are considered within the scope of "ionic liquid". The ionic liquids are a phosphonium-based, imidazolium-based, pyridinium-based, or a combination thereof, meaning the ionic liquids contain alkyl-substituted phosphonium, imidazolium, and or pyridinium cations. Examples of phosphonium-based, imidazolium-based, and pyridinium-based ionic liquids are discussed above.

The materials used herein were acquired from the following sources. Trihexyltetradecylphosphonium tetrafluroborate (TTPT) and 1-methyl-3-octylimidazolium chloride (MOIC), were obtained from Fluka (Seelze, Germany). Bis[(3-methyldimethoxysilyl)-propyl]polypropylene oxide (BMPO) was obtained from Gelest Inc. (Morrisville, Pa.). Fused silica capillary (250 µm i.d.) with a protective polyimide external coating was bought from Polymicro Technologies (Phoenix, Ariz.). Trifluoroacetic acid (TFA, 99%), nonanol, decanol, and undecanol, were secured from Acros Organics (Morris Plains, N.J., USA). Phenols (2,4,6-trichlorophenol, 2-tert-butyl-4-methoxyphenol, pentachlorophenol), aliphatic acids (nonanoic acid, decanoic acid, and undecanoic acid), aldehydes (decanal, undecanal, and dodecanal), ketones (hexanophenone, heptanophenone, decanophenone), anilines (N-butylaniline, diphenylamine, and acridine), PAHs (acenaphthene, phenanthrene, and pyrene), tetraethoxysilane (TEOS, 99%), and PDMDPS, dodecanal, hexanophenone, heptanophenone, methyltrimethoxysilane (MTMS 98%), tetramethoxysilane (TMOS), formic acid (96%), PEG MW 600, and poly(methylhydrosiloxane) (PMHS) were acquired from Sigma-Aldrich (St. Louis, Mo., USA). Methylene chloride, methanol, Kimwipes, polypropylene microcentrifuge tubes (2.0 mL), and glass scintillation vials (6 mL) were purchased from Fisher Scientific. Silanol-terminated PDMS was obtained from United Chemical Technologies (Bristol, Pa., USA). Poly-THF was a gift from BASF (Parsippany, N.J., USA). TTPT and BMPT were purchased from Fluka (Seelze, Germany). Chemical structures of sol solution components are illustrated in Table 1.

Nanopure deionized water (15.5 MΩ) was acquired using a Barnstead model 04741 Nanopure system (Barnstead International, Dubuque, Iowa, USA). Sol solution ingredients were mixed using a Fisher model G-560 Vortex Genie 2 (Fisher Scientific, Pittsburgh, Pa., USA). Sol solutions were centrifuged with a Micromax Thermo IECOM3590 microcentrifuge (NeedhamHeights, Mass., USA). A gas pressure-operated filling purging device (Hayes & Malik, J. Chromatogr. B 695 (1997) 3) was used to introduce a sol solution into, and to expel the solutions from, fused silica capillaries, and to pass helium (He) through the capillaries. A liquid sample dispenser (Bigham, et al., Anal. Chem. 74 (2002) 752) was used to facilitate gravity-fed flow of aqueous samples through the sol-gel microextraction capillary. An oxyacetylene torch (Smith Equipment, Watertown, S.D., USA) was used to flame seal fused-silica microextraction capillaries. An in-house designed liquid sample dispenser (Baltussen, et al., J. Microcolumn September 11 (1999) 737) was used to facilitate the gravity-fed flow of aqueous samples through the sol-gel microextraction capillary. A Shimadzu model GC-17 capillary gas chromatograph equipped with a flame ionization detector (FID) (Shimadzu, Kyoto, Japan) was used for CME-GC experiments. ChromPerfect for Windows (version 3.5) computer software (Justice Laboratory Software, Denville, N.J., USA) was used for on-line data collection and processing. SEM images were obtained with a Hitachi model S-800 scanning electron microscope (Hitachi, Tokyo, Japan).

TABLE 1

Names, functions, and chemical structures of sol-gel ingredients
used to prepare ionic liquid-mediated sol-gel CME coatings.

| Ingredient | Function | Chemical Structure |
| --- | --- | --- |
| Hydroxy-terminated Poly(dimethylsiloxane) | Sol-gel active organic ligand | $HO-Si(CH_3)_2-O-[Si(CH_3)_2-O]_n-Si(CH_3)_2-OH$ |
| Poly(tetrahydrofuran) 250 (PolyTHF) | Sol-gel active organic ligand | $HO-[(CH_2)_4-O]_n-H$ |
| Bis [(3-methyldimethoxysilyl)-propyl] Polypropylene Oxide (BMPO) | Sol-gel-active organic ligand | $H_3C-Si(OCH_3)_2-(CH_2)_3-O-[CH_2-CH(CH_3)-O]_n-(CH_2)_3-Si(OCH_3)_2-CH_3$ |
| Poly(ethylene glycol) MW 600 (PEG) | Sol-gel active organic ligand | $HO-(CH_2-CH_2-O)_n-H$ |
| Poly(dimethylsiloxane-co-diphenylsiloxane), dihydroxyterminated (PDMDPS) | Sol-gel active organic ligand | $HO-[Si(CH_3)_2-O]_x-[Si(C_6H_5)_2-O]_x-H$ |
| Trihexyltetradecylphosphonium Tetrafluoroborate (TTPT) | Co-Solvent | $[H_3C(CH_2)_5]_3P^+-(CH_2)_{13}CH_3 \; BF_4^-$ |
| 4-Methyl-N-butylpyridinium tetrafluoroborate (BMPT) | Co-Solvent | 4-methyl-1-butylpyridinium $BF_4^-$ |
| 1-Methyl-3-octylimidazolium chloride (MOIC) | Co-Solvent | 1-methyl-3-octylimidazolium $Cl^-$ |
| Methylene chloride | Co-Solvent | $CH_2Cl_2$ |
| Tetraethyl orthosilicate (TEOS) | Sol-gel precursor | $Si(OCH_2CH_3)_4$ |
| Poly(methylhydrosiloxane) (PMHS) | Deactivating Agent | $H_3C-Si(CH_3)_2-O-[Si(CH_3)(H)-O]_n-Si(CH_3)_2-CH_3$ |
| Trifluoroacetic Acid (TFA) 99% | Catalyst | $CF_3COOH$ |

Example 1

PDMS, BMPO, or polyTHF was individually weighed into a clean microcentrifuge tube in the amount shown in Table 2. In all cases, a mixture of 250 μL of methylene chloride and 50 μL of ionic liquid, TTPT or MOIC, was added.

Next, TEOS (50 μL) and PMHS (10 μL) were added in sequence for PDMS. In the case of poly-THF, PDMDSP, and BMPO sol-gels no PMHS was added, as seen in Tables 2 and 3. This was followed by the addition of 50 μL TFA 99%. After the addition of each chemical ingredient, the solution was vortexed for 1 min to ensure thorough mixing. The sol solution was further centrifuged for 4 min at 14,000 rpm (18,297× g). The supernatant was decanted into a clean microcentrifuge tube. Sol-gels without ionic liquid (PDMS-no IL, polyTHF-no IL, PDMDPS-no IL, and BMPO-no IL) were prepared in a similar manner except that 300 μL of $CH_2Cl_2$ was used as solvent instead of a mixture of $CH_2Cl_2$ (250 μL) and TTPT (50 μL). An ionic liquid-mediated PEG sol-gel (PEG-IL) and a PEG sol-gel that did not contain IL (PEG-no IL) were prepared in analogous manner using the ionic liquid BMPT (147.8 μL), methanol (40 μL), water (25 μL), MTMS (100 μL), TMOS (50 μL), and formic acid (61.8 μL).

TABLE 2

Compositions of sol-gel with TTPT ionic liquid (PDMS-IL, polyTHF-IL, or BMPO-IL) and without the ionic liquid (PDMS-no IL, polyTHF-no IL, or BMPO-no IL) used to prepare microextraction capillaries.

| Ingredient | Sol-gel PDMS coating | | Sol-gel polyTHF coating | | Sol-gel BMPO coating | |
| --- | --- | --- | --- | --- | --- | --- |
| | with IL | no-IL | with IL | no-IL | with IL | no-IL |
| PDMS (g) | 0.0505 | 0.0510 | 0 | 0 | 0 | 0 |
| BMPO (g) | 0 | 0 | 0 | 0 | 0.0507 | 0.0502 |
| polyTHF (g) | 0 | 0 | 0.025 | 0.025 | 0 | 0 |
| TTPT (μL) | 50 | 0 | 50 | 0 | 50 | 0 |
| $CH_2Cl_2$ (μL) | 250 | 300 | 250 | 300 | 250 | 300 |
| TEOS (μL) | 50 | 50 | 50 | 50 | 50 | 50 |
| PMHS (μL) | 10 | 10 | 0 | 0 | 0 | 0 |
| TFA 99% (μL) | 50 | 50 | 50 | 50 | 50 | 50 |

TABLE 3

Compositions of sol-gels with ionic liquid (BMPO-TTPT, BMPO-MOIC, and PDMDPS-MOIC) and without ionic liquid (BMPO-no IL and PDMDPS-no IL) without ionic liquid used to prepare microextraction capillaries.

| Ingredient | Sol-gel BMPO coating | | | Sol-gel BMPO coating | |
| --- | --- | --- | --- | --- | --- |
| | TTPT | MOIC | no-IL | MOIC | no-IL |
| BMPO (mg) | 50 | 50 | 50 | 0 | 0 |
| PDMDPS (mg) | 0 | 0 | 0 | 50 | 50 |
| TTPT (μL) | 50 | 0 | 0 | 0 | 0 |
| MOIC (μL) | 0 | 50 | 0 | 50 | 0 |
| $CH_2CH_2$ (μL) | 250 | 250 | 300 | 250 | 300 |
| TEOS (μL) | 50 | 50 | 50 | 50 | 50 |
| TFA 99% (μL) | 50 | 50 | 50 | 50 | 50 |

The main reactions that take place in the sol solution include hydrolysis of the sol-gel precursor(s) and polycondensation of sol-gel active species (Brinker & Scherer, Sol-Gel Science: The Physics and Chemistry of Sol-Gel Processing, Academic Press, San Diego, 1990). These reactions occur simultaneously and are affected by various experimental factors such as water content, type of catalyst used, precursor identity, nature of solvent(s) and other additives (e.g. organic molecules), (Mackenzie & Ulrich, Ultrastructure Processing of Advanced Ceramics, Wiley, New York, 1988). In this case, TFA was used as the catalyst for sol-gel PDMS, polyTHF, or BMPO coatings, while formic acid was used as a catalyst for the sol-gel PEG coatings. No extra water was added to the systems that utilized TTPT as (1) it created a phase separation in PDMS-IL and (2) sol-gel systems that contained BMPO gelled instantly in its presence. Trace amounts of water in the TFA and the methylene chloride were enough to initiate the hydrolysis of the sol-gel precursor. Water, generated from the condensation of those hydrolyzed products further facilitated the hydrolysis reaction.

Sol-gel reactions allowed polymeric chains of BMPO or PDMDPS to become chemically incorporated in the sol-gel network as an organic component of the organic-inorganic hybrid coating, and also to covalently anchor the coating to the inner surface of a fused silica capillary.

ILs were used as co-solvents and as porogens in the sol-gel system. Advantages of using ILs as solvents for reactions include their ability to be recycled, high thermal stability, and the improved stability of reactants in ILs (Liu, et al., Chem. Commun. 13 2005) 1778). Advantages of using ILs as porogens instead of organic molecules in sol-gel systems include the effect that the cation and the anion portions of the IL have on pore structure and distribution (Zhou, et al., Nano Lett. 4 (2004) 477; Klingshirn, et al., J. Mater. Chem. 15 (2005) 5174; Adams, et al., J. Chem. 54 (2001) 679; Zhang, et al., Micropor. Mesopor. Mater. 119 (2009) 97), and the ability of ILs to decompose from sol-gel systems without leaving residues behind (Klingshirn, et al., J. Mater. Chem. 15 (2005) 5174).

Example 2

Ionic Liquid (TTPT)-Mediated Polar Sol-Gel Microextraction Capillaries: PEG, polyTHF, and BMPO The supernatant of the centrifuged sol solution produced in Example 1 was immediately utilized to coat the capillaries. For each sol-gel composition, a hydrothermally treated (Hayes, PhD Dissertation, University of South Florida, Tampa, Fla., 2000) fused-silica capillary (50 cm×250 μm i.d.) was installed on a home-built filling purging device (Hayes & Malik, J. Chromatogr. B 695 (1997) 3). The capillary was filled with the sol solution using helium (20 psi; $1.38 \times 10^5$ Pa) until full. After several drops of the coating sol solution dripped out of the capillary, its exit end was sealed with a rubber septum. The solution was allowed to reside inside the capillary for 20 min to facilitate the formation of a surface-bonded sol-gel coating. After this in-capillary residence period, the rubber septum was removed from the capillary end and the un-bonded bulk sol solution was expelled from the capillary under helium pressure.

For the TTPT ionic liquid-mediated sol-gel coatings, the capillaries were purged under 20 psi ($1.38 \times 10^5$ Pa) helium pressure for 60 min prior to thermal conditioning which was somewhat different for coatings with different organic ligands. The sol-gel PDMS coated capillaries were thermally conditioned in a GC oven under He purge (1 mL min) from 40° C. to 300° C. at 1° C. min and were held at 300° C. for 300 min. The polyTHF and BMPO sol-gel coated capillaries were conditioned to a final temperature of 250° C. and 280° C., respectively, using the same temperature program.

The conditioned capillaries were rinsed with 2 mL of 1:1 (v/v) $CH_2Cl_2/CH_3OH$ mixture to remove any residual IL or its decomposition products. The capillaries were further dried under helium purge in a GC oven by raising the temperature from 40° C. to 300° C. (for PDMS), 250° C. (for polyTHF), or 280° C. (for BMPO) at a rate of 10° C./min and holding at the final temperature for 30 min.

For the BMPT ionic liquid-mediated sol-gel PEG capillaries were flame sealed with an oxy-acetylene torch, and then thermally conditioned in a GC oven from 40° C. to 110° C. at 5° C./min holding at 110° C. for 100 min. Following this, the ends of the capillaries were cut open with an alumina wafer, and rinsed with a 2 mL mixture of $CH_2Cl_2/CH_3OH$ (1:1, v/v) using 5 psi ($3.45 \times 10^4$ Pa) helium in the filling purging device to remove any remaining ionic liquid. The capillaries were further conditioned under He purge (1 mL min) in a GC oven by programming the temperature from 40° C. to 250° C. at 1° C. min, and was held at 250° C. for 120 min.

The sol-gel coated capillaries prepared without ionic liquid (TTPT or BMPT) were thermally conditioned analogous to their IL-mediated counterparts for comparative purposes. The conditioned sol-gel capillaries were then cut into 11-cm long pieces that were further used for capillary microextraction. Fragments of the sol-gel networks evolving in the vicinity of the fused-silica capillary inner walls had the opportunity to become covalently bonded to it via condensation reactions with silanol groups on the fused-silica capillary inner surface, as seen in FIGS. 1(A) and (B).

Example 3

Extraction Profiles and Characteristics of Ionic Liquid (TTPT)-Mediated Sol-Gel Microextraction Capillaries: PEG, polyTHF, and BMPO Capillaries produced as described in Example 2 were analyzed. A CME-GC analysis was conduced with aqueous samples, which were prepared using compounds from various chemical classes (aliphatic alcohols, aliphatic aldehydes, aromatic ketones, and polycyclic aromatic hydrocarbons [PAHs]). For each analyte, a stock solution (10 mg/mL) was prepared in methanol and was stored in a surface deactivated 6 mL glass scintillation vial. Fresh aqueous samples were prepared prior to extraction by further diluting these stock solutions with DI water to ng/mL levels. CME was performed as previously described (Bigham, et al., Anal. Chem. 74 (2002) 752). Briefly, an 11-cm long sol-gel coated microextraction capillary was vertically connected to the bottom of the empty gravity-fed sample dispenser (Bigham, et al., Anal. Chem. 74 (2002) 752). Liquid sample (15 mL) was then loaded into the dispenser from the top and allowed to flow through the capillary under gravity for 45 min. The capillary was then disconnected from the dispenser and any remaining solution was removed from the capillary by touching the end of the capillary with Kimwipes tissue paper. The microextraction capillary was then installed in the GC injector such that approximately 9 cm of the sol-gel capillary remained inside the GC injection port previously cooled down to 40° C., and approximately 2 cm of it protruded into the GC oven. This was accomplished by providing a gas-tight connection of the capillary with the lower end of the injection port with the help of a nut and a graphite ferrule. The lower free end of the microextraction capillary, located inside the GC oven, was connected to one end of a two-way press-fit fused-silica connector. Further, a Restek Crossbond 14% cyanopropylphenyl-86% PDMS 15 m×0.25 mm i.d. GC column inlet was attached to the other end of the connector. The extracted analytes, residing in the sol-gel coating of the microextraction capillary, were then thermally desorbed from the capillary by rapidly raising the temperature (60° C./min) of the injection port from 40° C. to 300° C. for the sol-gel PDMS, from 40° C. to 250° C. for the sol-gel PEG and polyTHF, and from 40° C. to 280° C. for the sol-gel BMPO coated microextraction capillaries. Desorption of the analytes was performed in the splitless injection mode, keeping the split closed for the entire CME-GC analysis. The desorbed analytes were swept onto the GC column by the carrier gas flow and were focused at the inlet of the GC column maintained at 35° C. Following this, the GC oven temperature was programmed from 35° C. (1 min) to 270° C. at a rate of 20° C. min to achieve separation of the extracted analytes transferred to the GC column. The column was held at a final temperature of 250° C. when sol-gel PEG or polyTHF microextraction capillaries were used. Analytes were detected using FID at 350° C.

Figure 2:
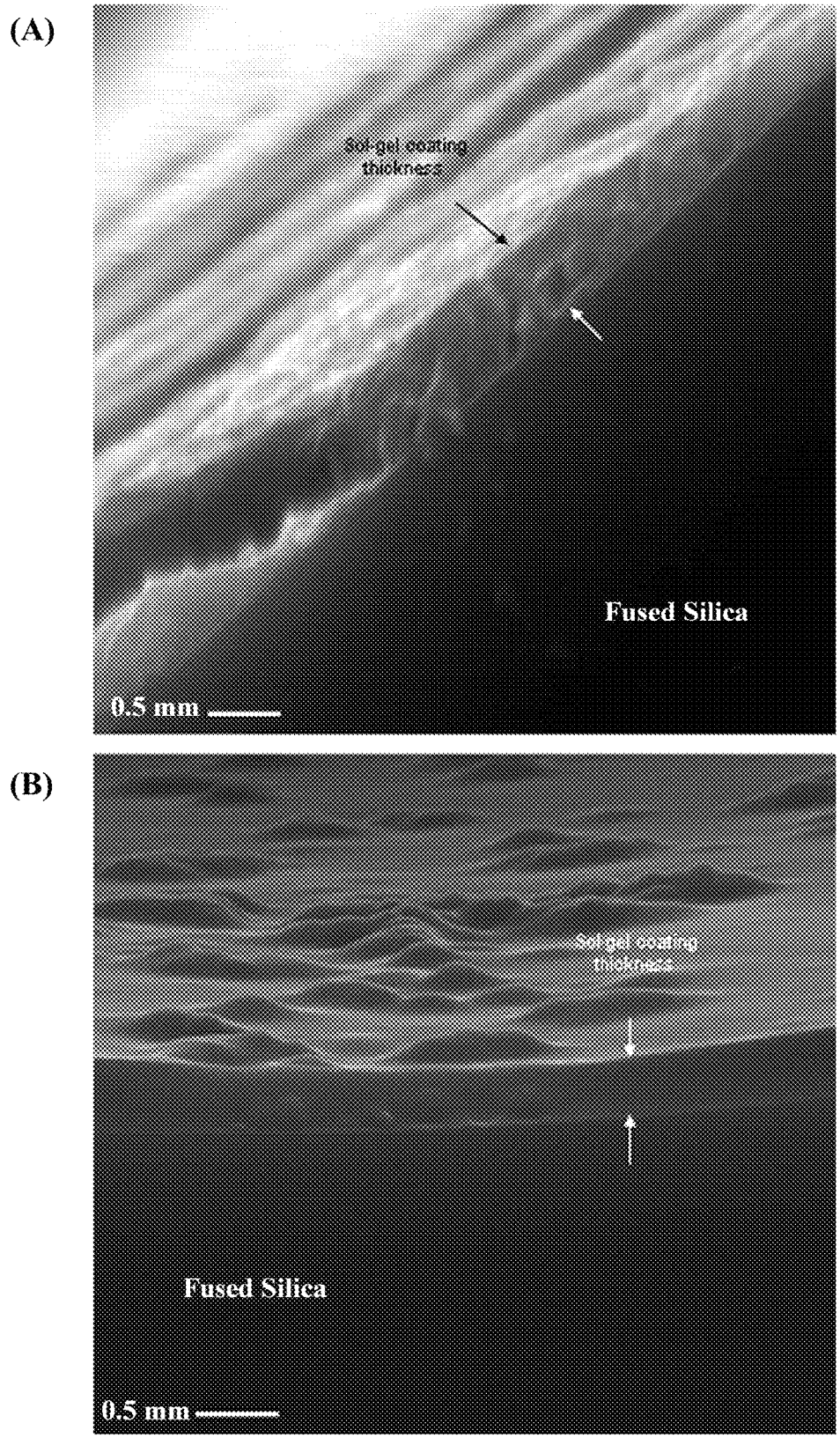
FIGS. 2(A) and (B) are scanning electron microscopic images of cross-sections of 250 μm i.d. (A) sol-gel PDMS-IL (22000×) and (B) sol-gel PDMS-no IL (20000×) coated microextraction capillaries.

Scanning electron microscopy (SEM) was used to investigate the morphology of the PDMS-IL and PDMS-no IL sol-gel coatings, as seen in FIGS. 2(A) and (B). The IL-mediated sol-gel microextraction capillaries were rinsed with a 2 mL mixture (1:1, v/v) of methylene chloride and methanol prior to acquiring SEM images. Rinsing removed any debris and unbonded chemicals from the thermally conditioned coating leaving the chemically bonded sol-gel coating on the surface. Since the analytical data was collected after rinsing, it is obvious that the all of the sol-gel coatings survived rinsing and were solvent stable. As the SEM images show, the ionic liquid-mediated sol-gel coating, seen in FIG. 2(A), appears to have a more porous texture than the PDMS-no IL coating, seen in FIG. 2(B). This is an indication that the IL TTPT affected the structure of the overall sol-gel.

In the case of the PDMS sol-gels, the addition of phosphonium-based IL, TTPT, slowed down the gelation by about 1.5 h in comparison with the sol-gel that did not contain the IL. These results are in agreement with those of Karout and Pierre (Karout & Pierre, J. Non-Cryst. Solid 353 (2007) 2900) who also observed an increase in gelation time due to the increase in relative amounts of pyridinium-based and imidazolium-based ILs in sol-gel systems. The slower gelation in the ionic liquid-mediated sol-gels can be attributed to the increased viscosity of the sol solution due to the addition of the IL. The kinematic viscosity of TTPT is 1117.80 $mm^2$ $s^{-1}$ (Merck, Ionic Liquids: New Materials for New Applications, Merck KGaA, Darmstadt, Germany, 2009) compared to that of methylene chloride which is 0.3298 $mm^2$ $s^{-1}$ (California Environmental Protection Agency: Air Resources Board, 2009). Further, it is reasonable to assume that the IL did not play a role in extractions since the thermal decomposition temperature of TTPT is 190° C. (Merck, Ionic Liquids: New Materials for New Applications, Merck KGaA, Darmstadt, Germany, 2009), and the ionic liquid-mediated sol-gel PDMS microextraction capillaries were heated in an inert environment to 300° C. Therefore, it can be safely assumed that during thermal conditioning, the IL had decomposed and the decomposition products were at least partially removed from the capillary with the purging helium flow. Any remaining products of the decomposition were further removed from the capillary during the rinsing step.

Figure 3:
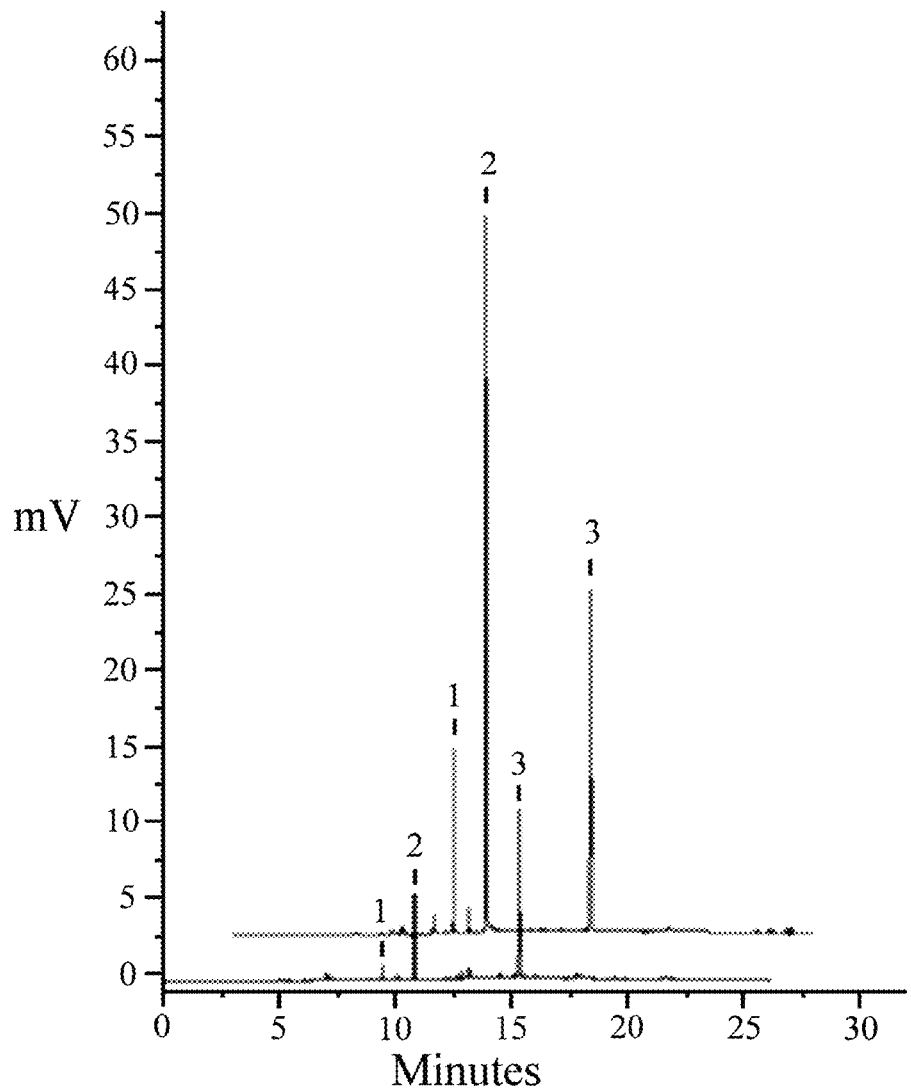
FIG. 3 is a composite graph comparing the CME-GC analysis of 125 ppb dodecanal, 100 ppb heptanophenone, and 50 ppb pyrene on (top plot) sol-gel PDMS-IL and (bpttom plot) sol-gel PDMS-no IL microextraction capillaries. Extraction conditions: 11 cm×0.25 mm i.d. microextraction capillary; extraction time of 45 min (gravity fed at room temperature). Other conditions: 15 m×0.25 mm i.d. Restek Crossbond® 14% cyanopropylphenyl-86% PDMS coated GC column; splitless desorption; injector temperature was 300° C.; programmed temperature GC run from 35° C. (1 min) to 270° C. at a rate of 20° C./min; helium carrier gas: FID 350° C. Peaks: (1) dodecanal, (2) heptanophenone, and (3) pyrene for both chromatograms.

The pre-concentration abilities of the two types of sol-gel PDMS capillaries (PDMS-IL and PDMS-no IL) were compared to determine the effect of the IL on the resulting sol-gel sorbent. Extraction of an aqueous sample containing 125 ppb dodecanal, 100 ppb heptanophenone, and 50 ppb pyrene was performed on the two types of sol-gel capillaries. FIG. 3 shows two chromatograms representing extraction results obtained on sol-gel PDMS-IL and sol-gel PDMS-no IL capillaries, respectively. These chromatograms show that the sol-gel PDMS-IL coating provided significantly higher extraction utility than the PDMS-no IL. This, in turn, translates into lower detection limits for the sol-gel PDMS-IL microextraction capillary, as seen in Table 4.

TABLE 4

Peak area repeatability and limit of detection data for dodecanal (200 ppb sample), heptanophenone (100 ppb sample), and pyrene (50 ppb sample) extracted from aqueous samples using three replicate measurements by CME-GC using sol-gel immobilized PDMS microextraction capillaries prepared (A) with ionic liquid and (B) without ionic liquid.

| | Run-to run repeatability (n = 3) | | | | Detection limits (S/N = 3) | |
|---|---|---|---|---|---|---|
| | Sol-gel A | | Sol-gel B | | | |
| Analyte | Mean peak area[a] | RSD (%) | Mean peak area[a] | RSD (%) | Sol-gel A (ng/L) | Sol-gel B (ng/L) |
| Dodecanal | 129.0 | 5.0 | 4.6 | 14.1 | 17.4 | 487.0 |
| Heptanophenone | 265.3 | 4.2 | 17.2 | 6.4 | 3.9 | 52.3 |
| Pyrene | 69.6 | 4.5 | 45.5 | 2.8 | 3.2 | 4.9 |

[a]Arbitrary unit.

Run-to-run and capillary-to-capillary repeatability data were collected for each analyte on the two types of capillaries in individual CME-GC experiments, seen in Table 3. In all repeatability experiments, 500 ng mL dodecanal, 200 ng mL heptanophenone, and 50 ng mL pyrene aqueous samples were individually extracted using the two types of capillaries. Run-to-run GC peak area repeatability data was collected by extracting the sample analytes in individual experiments on each type of capillary using three replicate measurements. For all three analytes, the sol-gel PDMS-IL coated capillary provided consistent run-to-run RSD values between 4.0% and 5.0%. On the other hand, quite scattered RSD values (2.76% for pyrene, 6.45% for heptanophenone, and 14.1% for dodecanal) were obtained for the same analytes using the sol-gel PDMS-no IL coated capillary. This coating also provided worse limits of detection for all three analytes. Both sol-gel PDMS-IL and sol-gel PDMS-no IL coated capillaries provided significantly higher detection limits for dodecanal compared to pyrene and heptanophenone.

Capillary-to-capillary reproducibility data was obtained by extracting each sample in triplicate onto six individually prepared capillaries: three PDMS-IL and three with PDMS-no IL capillaries. This data characterized the reproducibility of the sol-gel coating method. The coatings prepared with ionic liquid (PDMS-IL) provided excellent capillary-to-capillary repeatability. Peak area RSD values of 2.26%, 0.15%, and 4.07% were obtained for dodecanal, heptanophenone, and pyrene, respectively. The sol-gel coating prepared without ionic liquid (PDMS-no IL) provided RSD values of 7.79% for heptanophenone and 9.72% for pyrene. Repeated extractions were made on the capillaries without deterioration of performance over a period of 9 months. Furthermore, the coating is solvent stable and can be rinsed to ensure consistent performance.

In CME-GC experiments, both types of sol-gel PDMS capillaries provided limits of detection (using a signal to noise ratio of 3) in the ng/L range. However, the sol-gel PDMS-IL microextraction capillary provided better detection limits (3.2-17.4 ng/L) than the sol-gel PDMS-no IL capillary (4.9-487.0 ng/L). This is likely because the sol-gel PDMS-IL capillary had a more porous morphology, as seen in FIGS. 2(A) and (B), and thereby provided a higher surface area for sorption. These results clearly suggest that the ionic liquid had a positive effect on the extraction ability of the sol-gel PDMS coating. Furthermore, PDMS sol-gel coatings are known to be thermally stable beyond 350° C. (Wang, et al., Anal. Chem. 69 (1997) 4566).

Figure 4:
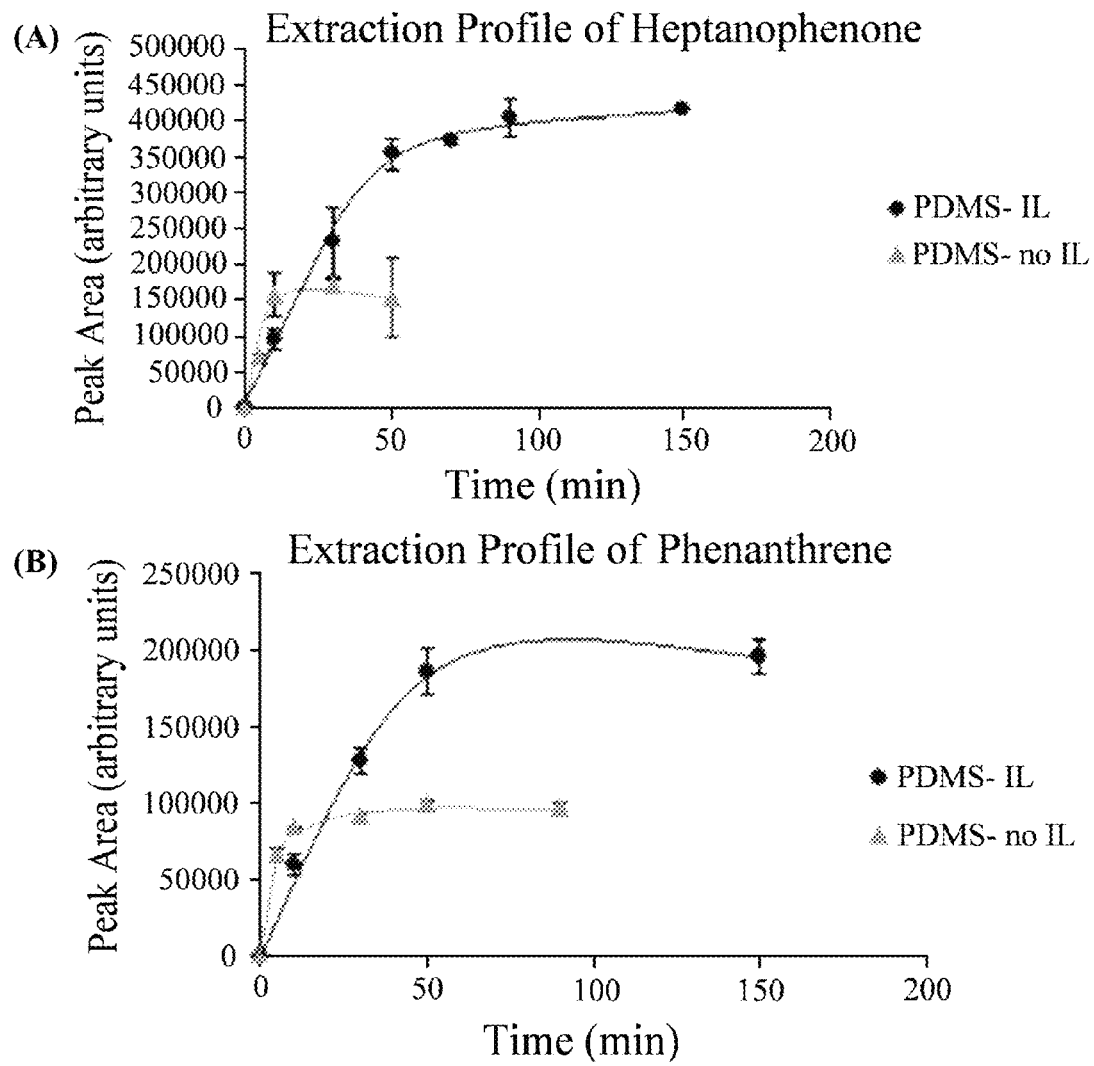
FIGS. 4(A) and (B) are extraction profiles of (A) heptanophenone and (B) phenanthrene extracted on 11 cm×0.25 mm i.d. PDMS-IL and PDMS-no IL sol-gel coated microextraction capillaries from an aqueous sample. Extraction conditions: triplicate extraction at various time intervals; microextraction capillaries were rinsed with 1:1 v/v $CH_2Cl_2$: methanol and dried at 300° C. before each extraction. GC analysis conditions: 15 m×0.25 mm i.d. Restek Crossbond® 14% cyanopropylphenyl-86% PDMS coated GC column; splitless desorption; injector temperature was 300° C.; programmed temperature GC run from 35° C. (1 min) to 270° C. at a rate of 20° C./min; helium carrier gas: FID 350° C.

Since CME is a non-exhaustive equilibrium extraction technique (Eisert & Pawliszyn, Anal. Chem. 69 (1997) 3140), it is important to determine the time required for the analyte to reach a sorption desorption equilibrium between the sol-gel coating and the sample. The extraction profiles of the PDMS-IL and PDMS-no IL capillaries were compared using heptanophenone, seen in FIG. 4(A), and phenanthrene, seen in FIG. 4(B), as test solutes. The extraction profiles seen in FIGS. 4(A) and (B) indicate that the PDMS-IL coating had a higher capacity, but the equilibrium is reached at a slower pace than on sol-gel PDMS-no IL coating. The extraction time required for the curve to reach the plateau indicates the onset of extraction equilibrium. Beyond this time no more analytes can be extracted. In the case of PDMS-no IL extraction time was 10-15 min for both analytes, but in the case of PDMS-IL the equilibrium was attained at about 60 min for both analytes. Thus, fewer experiments were required for PDMS-no IL since the equilibrium time was reached quickly. This extraction behavior on the ionic liquid-mediated coating can be explained by the slow diffusion of analytes in the liquid filling the porous sol-gel structure.

Figure 5:
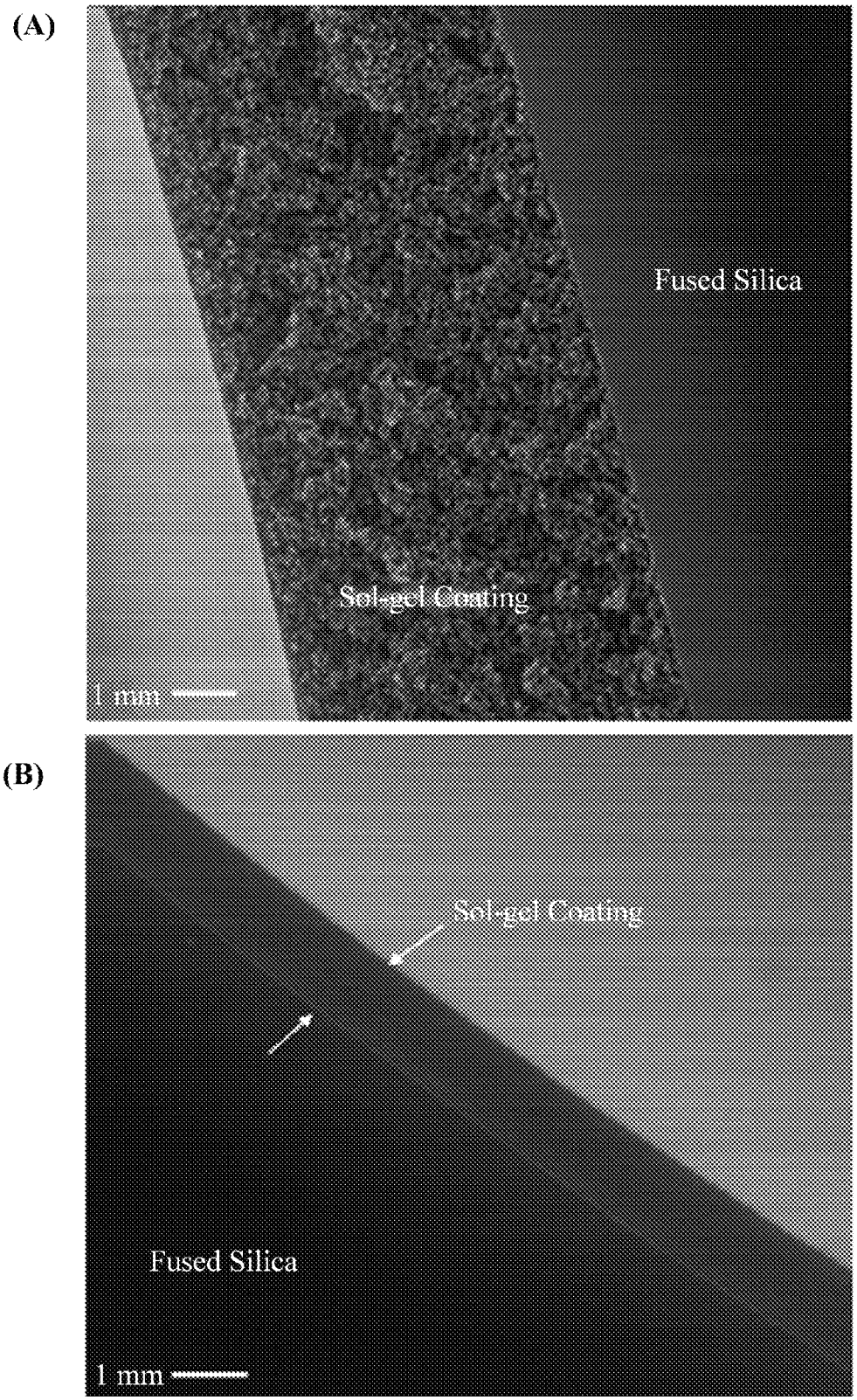
FIGS. 5(A) and (B) are scanning electron microscopic images of cross-sections of 250 μm i.d. (A) sol-gel PEG-IL (12,000×), (B) sol-gel PEG-no IL (15,000×), (C) sol-gel polyTHF-IL (500×), (D) sol-gel polyTHF-no IL (350×) coated microextraction capillaries.
Figure 5:
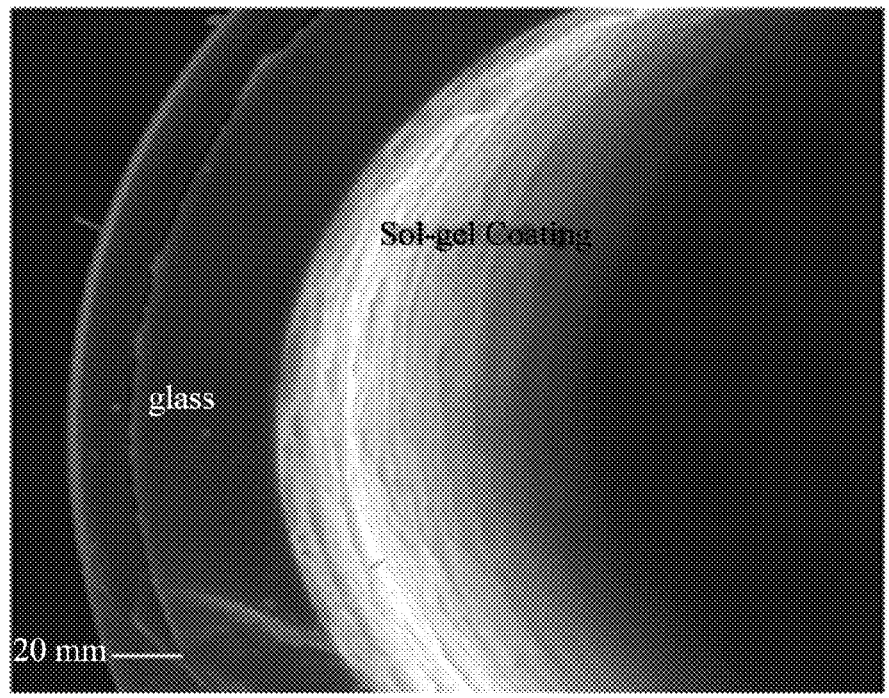
Figure 5:
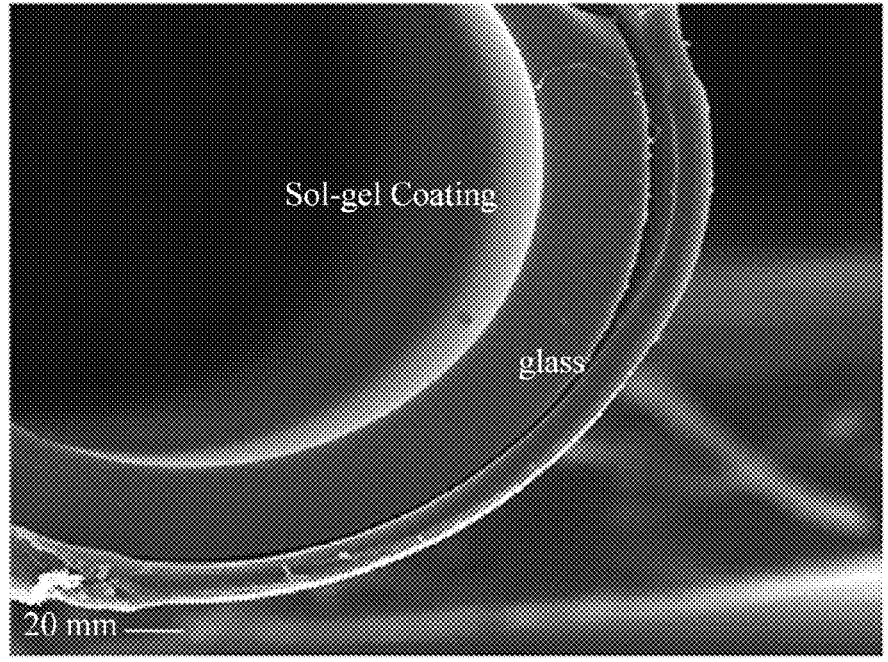
Figure 6:
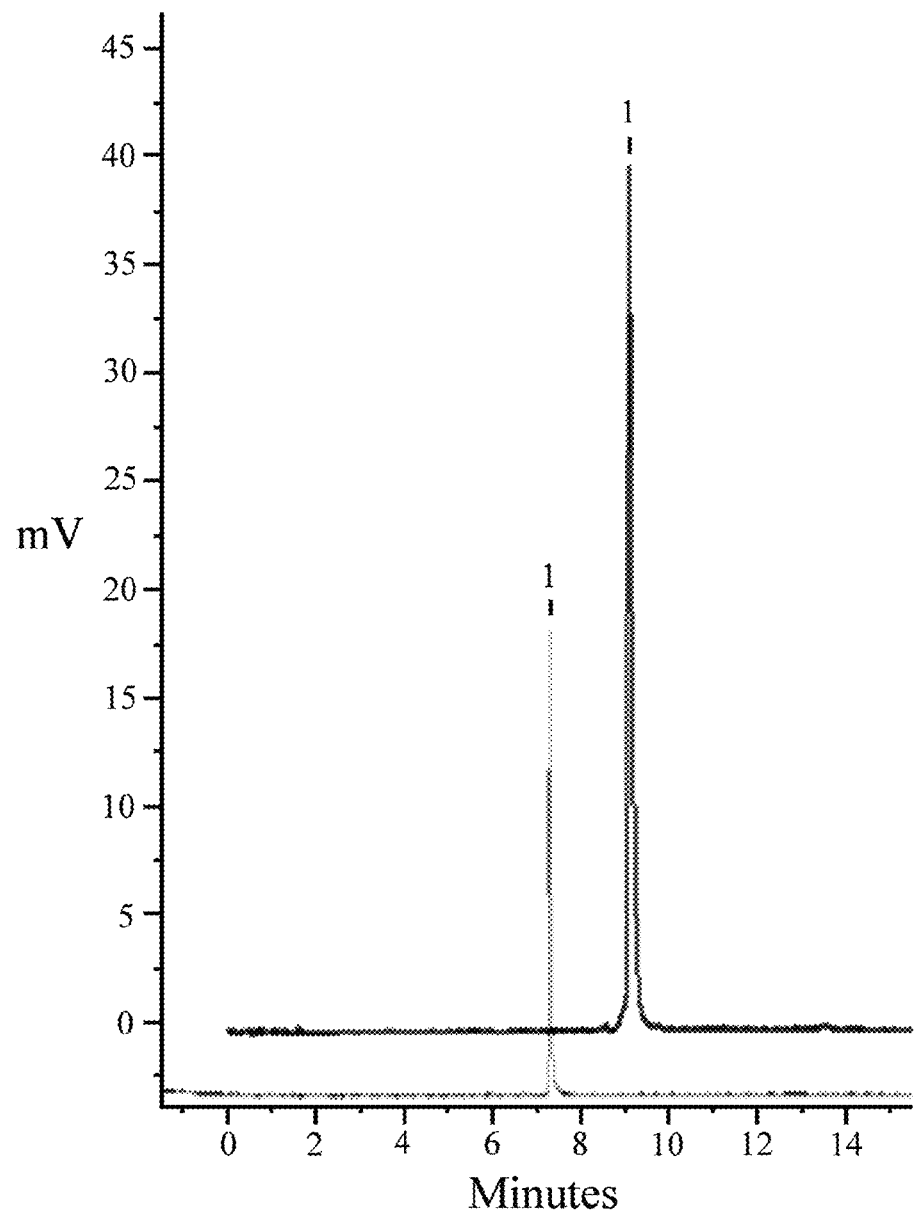
FIG. 6 is a composite graph comparing the CME-GC analysis of 100 ppb decanol (bottom plot) sol-gel PEG-IL and (top plot) sol-gel PEG-no IL microextraction capillaries. Extraction conditions were the same as FIG. 2. Other conditions: 15 m×0.25 mm i.d. Restek Crossbond® 14% cyanopropylphenyl-86% PDMS coated GC column; splitless desorption; injector temperature was 250° C.; programmed temperature GC run from 35° C. (1 min) to 250° C. at a rate of 20° C./min; helium carrier gas: FID 350° C. Peak: (1) decanol for both chromatograms.
Figure 7:
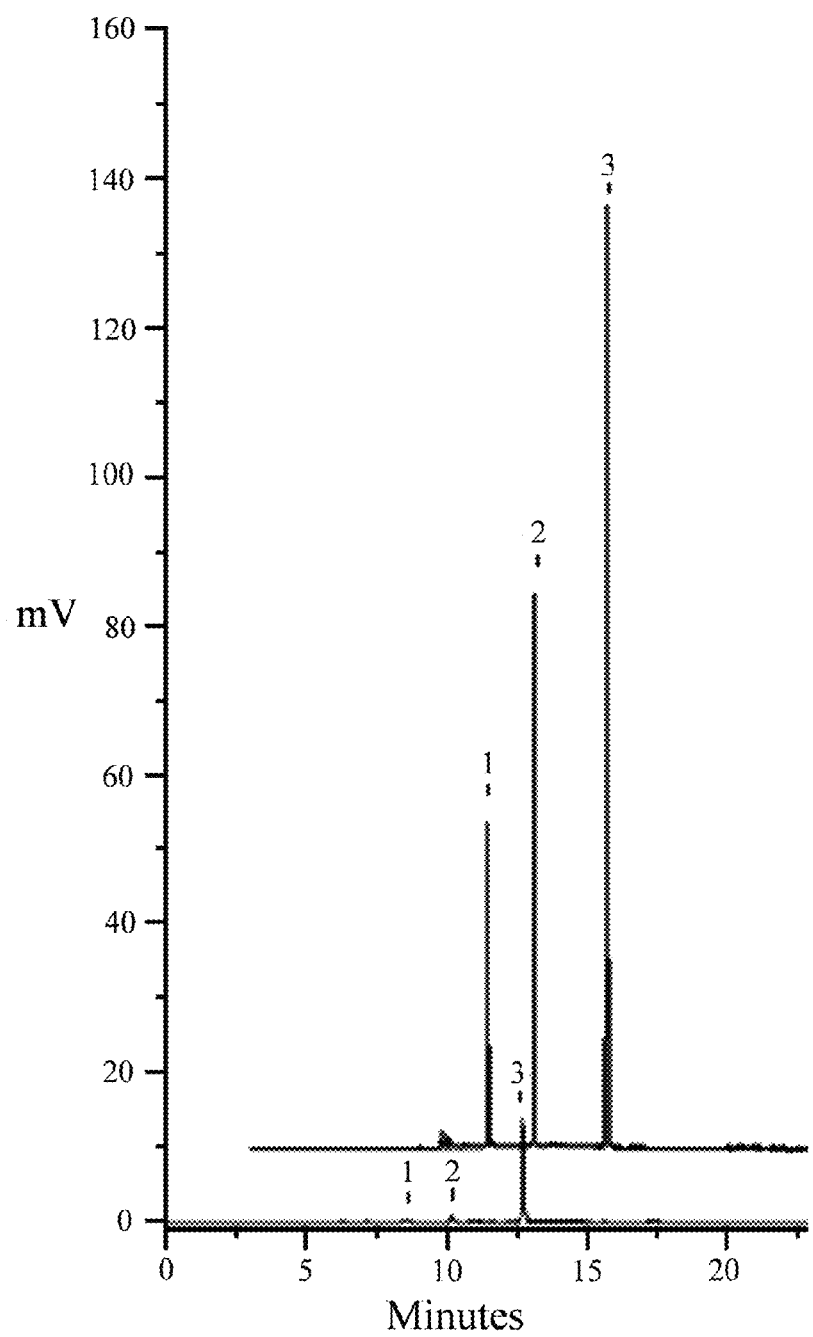
FIG. 7 is a composite graph comparing the CME-GC analysis of 500 ppb decanol, 500 ppb hexanophenone, 200 ppb phenanthreme (bottom plot) sol-gel PolyTHF-IL and (top plot) sol-gel PolyTHF-no IL microextraction capillaries. Extraction conditions were the same as FIG. 2. Other conditions were the same as FIG. 5. Peaks: (1) decanol, (2) hexanophenone, and (3) phenanthrene for both chromatograms.

Attempts were made to prepare ionic liquid-mediated polar sol-gel coatings based on PEG and polyTHF. BMPT was tested in conjunction with the PEG sol-gel coating, while TTPT was used to prepare the polyTHF sol-gel coating, and again sol-gel coatings were prepared for each polymer without ionic liqiod (no-IL). SEM was used to investigate the morphology of the sol-gel coated capillaries. Cross-sections of the capillaries showed that PEG-IL sol-gel coating, seen in FIG. 5(A), appeared more porous than its counterpart prepared without IL, seen in FIG. 5(B). The same trend was observed for the sol-gel polyTHF coatings; with sol-gel polyTHF-IL, seen in FIG. 5(C), observed more porous than sol-gel polyTHF-no IL, seen in FIG. 5(D). Reproducible coating thickness could be obtained with IL-mediated sol-gels. For example, three individually prepared PEG-IL sol-gel coated capillaries had an average thickness of 5.8 μm with a standard deviation of 0.3 μm (an RSD value of 5.2%). Sol-gel coatings with greater porous morphology obtained with the help of ILs were expected to provide better performance in extraction. However, extractions using the ionic liquid-mediated PEG and the polyTHF sol-gel porous coatings showed that this was not the case. The PEG-no IL, seen in FIG. 6 top plot, and the polyTHF-no IL, seen in FIG. 7 top plot, coated microextraction capillaries provided better performance in CME-GC. A peak area for 100 ppb decanol extracted on the sol-gel PEG-IL coating was 72,329 arbitrary units, and the peak area provided by the sol-gel PEG-no IL coating was 266,681 arbitrary units. As FIG. 7 shows, three analytes—decanol, hexanophenone, and phenanthrene—were poorly extracted on the polyTHF-IL microextraction capillary (bottom) compared to the polyTHF-no IL capillary (top). It appears that while the sol-gel PEGIL and polyTHF-IL coatings were more porous, they might have consisted mainly of silica with only very small amounts of polymer incorporated into the sol-gel network resulting in inferior extraction performance.

Even though, the PEG and the polyTHF sol-gel coated capillaries were prepared utilizing different ILs and different thermal conditioning methods, they both demonstrated that a C—OH terminated polymer does not create effective sol-gel sorbents when mediated by an IL. An important factor in this phenomenon is the lower reactivity of the terminal hydroxyl groups on PEG and poly-THF compared to silanol groups on hydroxy-terminated PDMS and alkoxy groups on silica-based sol-gel precursors (Huang & Wilkes, Synthesis, in: Wang & Zhang (Eds.), Handbook of Nanophase and Nanostructured Materials, vol. 1, Kluwer Academic Plenum Publishers, New York, 2003, p. 90). Because of higher reactivity of Si—OH and Si—OR groups compared with C—OH groups, polycondensation reactions are likely to predominantly take place between chemical species containing the sol-gel active Si—OH (silanol) and/or alkoxysilane groups. Condensation reactions between a Si—OH or a Si—OR group and the terminal C—OH (hydroxyl group) of the polymers can be expected to occur less effectively. Apparently, condensation of C—OH terminated polymers is slowed down even further or is hindered when utilizing an ionic liquid in the sol-gel system. While the ILs help develop porous morphology in coatings, they appear not to produce sol-gel coatings that are effective at microextraction due to quantitative deficiency of bonded organic polymer ligands. As was the case with the PDMS-based sol-gel sorbents, it can be assumed that the ILs played no role in extractions. As mentioned, this is because TTPT decomposes at 190° C. (Merck, Ionic Liquids: New Materials for New Applications, Merck KGaA, Darmstadt, Germany, 2009), and the capillaries prepared with this IL were conditioned at temperatures higher than 250° C., and they were rinsed with organic solvents before use. Although the decomposition temperature of BMPT is 295° C. (Merck, Ionic Liquids: New Materials for New Applications, Merck KGaA, Darmstadt, Germany, 2009), and the PEG capillaries prepared with it were conditioned at a lower temperature, this IL was removed from the capillary by rinsing with copious amounts of methylene chloride and methanol mixture.

In order to determine if in fact PEG and polyTHF were not being incorporated into the sol-gel network in the presence of an IL due to their low reactivity, a novel sol-gel system was investigated that contained (instead of PEG or polyTHF) bis[(3-methyldimethoxysilyl) propyl]polypropylene oxide (BMPO)—a polymer with sol-gel active methoxysilane termination and a flexible propylene oxide repeating unit, seen in Table 1. BMPO has not been utilized in the preparation of microextraction coatings. It has, however, been used previously to synthesize hybrid inorganic-organic polymer membranes (Li, et al., Electrochim. Acta 51 (2006) 1351). Two types of sol-gel BMPO coatings: (a) coatings prepared with the use of ionic liquid (TTPT) (BMPO-IL) and (b) coatings prepared without the use of TTPT (BMPO-no IL), shown in Table 2. The ionic liquid slowed the rate of gelation in the case of sol-gel BMPO system just like it did in the sol-gel PDMS system. BMPO-IL sol solution gelled in more than 24 h, and BMPO-no IL gelled in 16 h.

Figure 8:
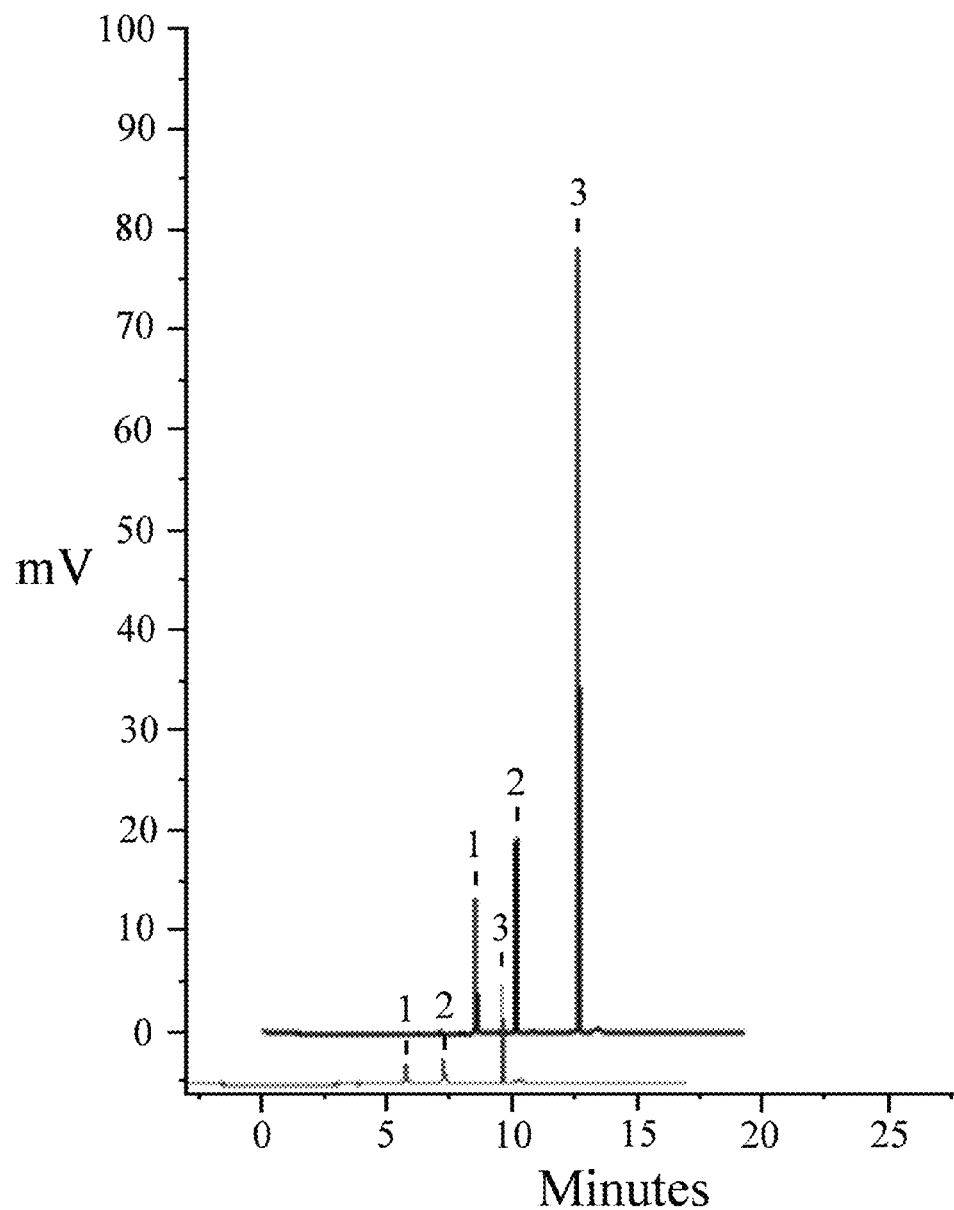
FIG. 8 is a composite graph comparing the CME-GC analysis of 500 ppb decanol, 500 ppb hexanophenone, and 200 ppb phenanthrene on (top plot) sol-gel BMPO-IL and (bottom plot) sol-gel BMPO-no IL microextraction capillaries. Extraction conditions were the same as FIG. 3. Other conditions: 15 m×0.25 mm i.d. Restek Crossbond® 14% cyanopropylphenyl-86% PDMS coated GC column; splitless desorption; injector temperature was 280° C.; programmed temperature GC run from 35° C. (1 min) to 270° C. at a rate of 20° C./min; helium carrier gas: FID 350° C. Peaks: (1) decanol, (2) hexanophenone, and (3) phenanthrene for both chromatograms.

As FIG. 8 shows, unlike the IL-mediated PEG and poly-THF sol-gel coated capillaries, the IL-mediated BMPO sol-gel, seen in FIG. 8 top plot, coated capillaries could extract analytes—decanol, hexanophenone, and phenanthrene—with significantly higher extraction efficiency than its non-IL counterparts, seen in FIG. 8 bottom plot. Compared to the BMPO-no IL sol-gel coating, the BMPO-IL sol-gel coating provided 3.6, 3.5, and 8.1 times more efficient extractions for decanol, hexanophenone, and phenanthrene, respectively. Since BMPO is a sol-gel active polymer that acquires Si—OH termination after hydrolysis, it gets effectively bonded into the sol-gel network, as depicted in FIG. 1(B), even in the presence of IL because of higher reactivity terminal silanol groups.

Limits of detection (using a signal to noise ratio of 3) for the investigated analytes in CME-GC-FID analysis were determined to be in the ng/L range for the BMPO-IL and BMPO-no IL capillaries. The BMPO-IL coating provided a limit of detection of 53.0 ng/L for decanol, 41.0 ng/L for hexanophenone, and 3.5 ng/L for phenanthrene. The BMPO-no IL capillary provided a limit of detection of 186.0 ng/L for decanol, 137.0 ng/L for hexanophenone, and 27.0 ng/mL for phenanthrene. Thus, the sol-gel BMPO-IL capillaries provided 3-5 times better detection limits than BMPO-no IL capillaries.

This work demonstrated the possibility of using ILs in the preparation of both non-polar (PDMS) and polar (BMPO) sol-gel coating for CME. In both the cases, the IL-mediated sol-gel coatings had significantly better extraction performance than analogous coatings prepared without ionic liquids. Thus, IL-mediated sol-gel coatings open new possibilities for effective preconcentration of analytes since both polar and non-polar sol-gel coatings can be prepared with ionic liquid mediation. However, when preparing non-polar or polar hybrid organic-inorganic sol-gel sorbents using ILs it is vital to choose organic polymers and sol-gel precursors with similar sol-gel reactivity to ensure that the organic polymers are effectively incorporated into the sol-gel network providing an efficient sol-gel sorbent.

Example 4

Ionic Liquid (TTPT, MOIC)-Mediated Sol-Gel Microextraction Capillaries

Figure 9:
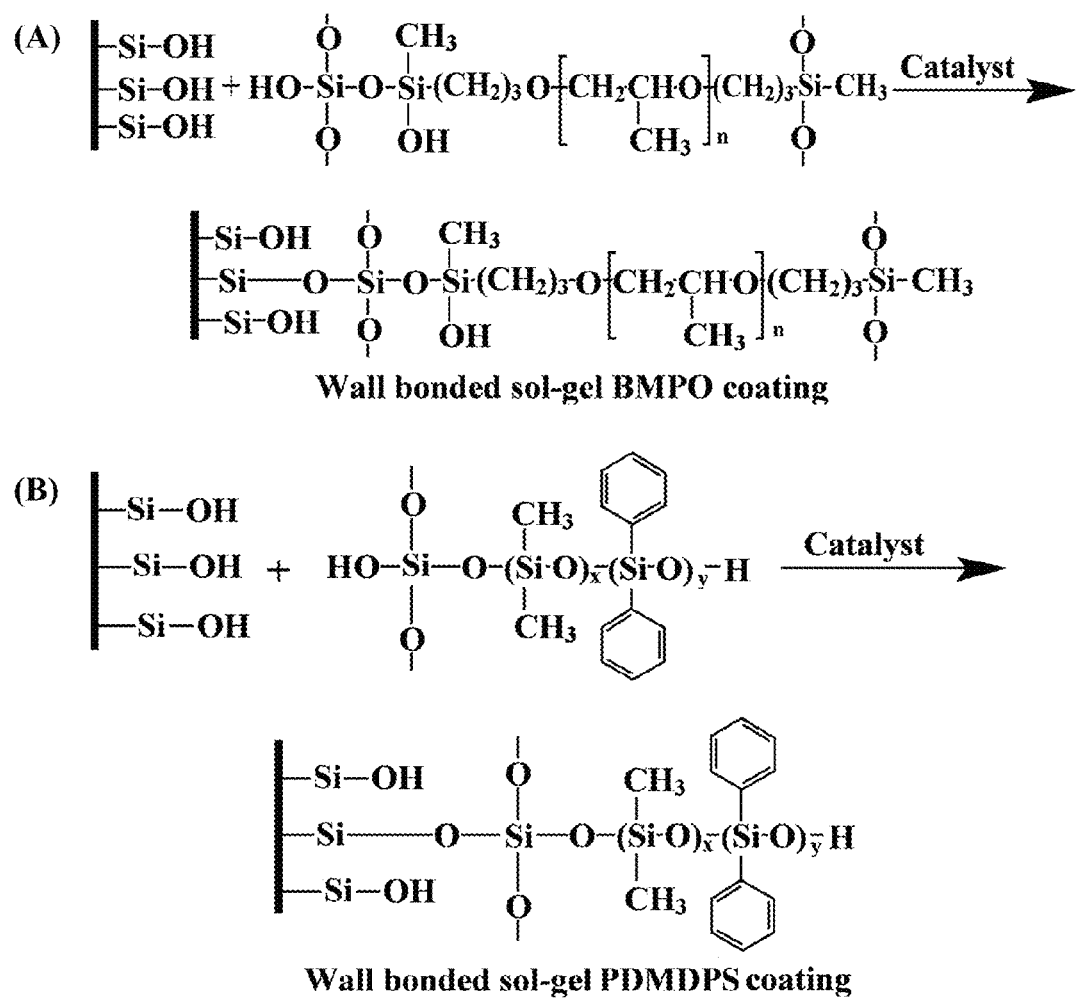
FIGS. 9(A) and (B) are reaction schemes depicting the polycondensation of 3D sol-gel network to fused silica capillary wall for (A) BMPO and (B) PDMDPS.

Hydrothermally treated (Hayes, Ph.D. Dissertation, University of South Florida, Tampa, Fla., 2000) fused silica tubing (50 cm×0.25 mm i.d.) was utilized to prepare sol-gel coated microextraction capillaries. The fused silica capillary was set up in the filling purging device (Hayes & Malik, J. Chromatogr. B 695 (1997) 3), and helium (20 psi; $1.38 \times 10^5$ Pa), as discussed in Example 2. The solution was kept in the capillary for 20 min allowing a surface-bonded sol-gel coating to form. Then any un-bonded sol solution was expelled from the capillary by purging with helium (20 psi; $1.38 \times 10^5$ Pa) for 60 min. Portions of the sol-gel BMPO, seen in FIG. 9(A), or PDMDPS, seen in FIG. 9(B), networks evolving near the fused silica capillary inner walls had the opportunity to become covalently bonded to it via condensation reactions with silanol groups on the capillary inner surface.

The BMPO sol-gel capillaries (prepared with or without IL-mediation as indicated in Example 1) were thermally conditioned under helium purge in a GC oven from 40° C. to 280° C. at 1° C. min and were held at the final temperature for 300 min. The sol-gel PDMDPS capillaries (prepared with or without IL-mediation) were thermally conditioned using a temperature programming rate of 1° C./min to a final temperature of 300° C. for 300 min. The conditioned capillaries were rinsed with 2 mL of 1:1 (v/v) methylene chloride methanol mixture and were dried under helium purge in a GC oven by programming the temperature from 40° C. to 280° C. (for BMPO) or 300° C. (for PDMDPS) at 10° C./min, holding at a final temperature for 30 min. The finished sol-gel coated capillaries were then chopped into 11-cm long pieces; they were further used for CME.

Example 5

Extraction Profiles and Characteristics of Ionic Liquid (TTPT, MOIC)-Mediated Sol-Gel Microextraction Capillaries Stock solutions (10 mg mL) of test analytes from various chemical classes (phenols, acids, amines, alcohols, aldehydes, ketones, and PAHs) were prepared in methanol and were stored in glass scintillation vials. Aqueous test samples were prepared by diluting the stock solutions to ng/mL levels with Nanopure water. CME experiments were conducted as earlier detailed (Bigham, et al., Anal. Chem. 74 (2002) 752). Briefly, an 11-cm long sol-gel coated microextraction capillary was vertically connected to the bottom of the empty gravity-fed sample dispenser. Liquid sample (15 mL) was allowed to flow through the sol-gel microextraction capillary under gravity for 45 min. Following this, the capillary was removed from the dispenser, and the microextraction capillary was installed in the GC injector. About 9 cm of the sol-gel capillary was contained inside the GC injection port (which was held at 40° C.). Only a 2-cm segment of the capillary remained in the GC oven. This was enabled by a gas-tight connection of the capillary to the lower end of the GC injection port. The portion of the microextraction capillary that was inside the GC oven was connected to one end of a two-way press-fit fused silica connector. The inlet of a Restek Crossbond 14% cyanopropylphenyl-86% PDMS GC column (15 m×0.25 mm i.d.) was coupled to the other end of the connector. Analytes that were extracted onto the sol-gel coating of the microextraction capillary were then thermally desorbed from the capillary. This was accomplished by rapidly raising the temperature (60° C./min) of the injection port from 40° C. to 280° C. for the sol-gel BMPO and to 300° C. for the sol-gel PDMDPS coated microextraction capillaries. Analytes were desorbed in the splitless injection mode, and the split was kept closed for the entire CMEGC analysis. The mobile phase transferred the desorbed analytes onto the GC column, and they were focused at the inlet of the GC column maintained at 35° C. The GC oven temperature was then programmed from 35° C. (1 min) to 270° C. at a rate of 20° C./min to achieve chromatographic separation of the desorbed analytes that were further detected by an FID maintained at 350° C.

Figure 10:
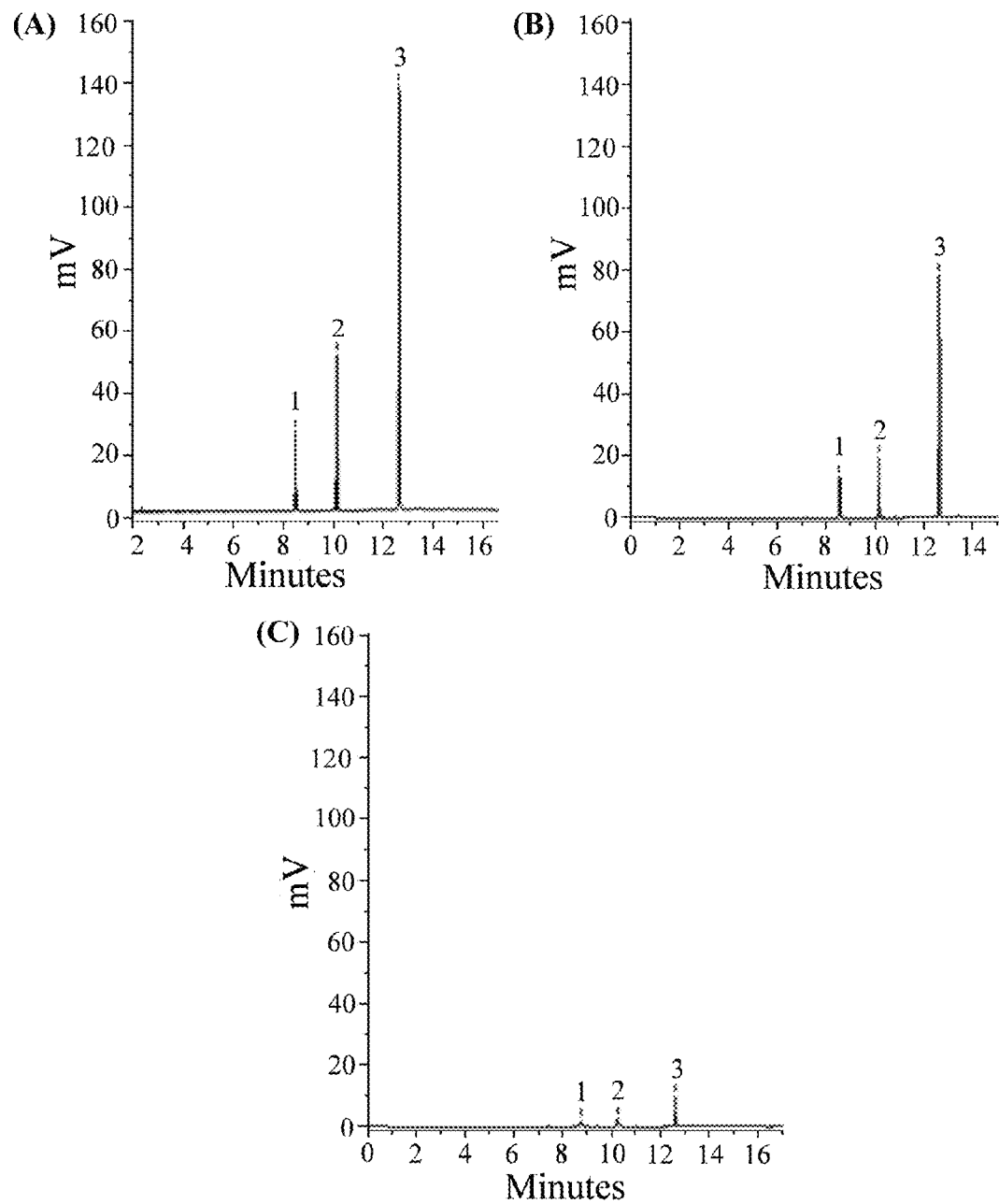
FIGS. 10(A), (B) and (C) are graphs comparing the CME-GC analysis of 500 ppb decanol, 500 ppb hexanophenone, and 200 ppb phenanthrene on (A) MOIC-mediated sol-gel BMPO, (B) TTPT-mediated sol-gel BMPO; and (C) sol-gel BMPO-no IL microextraction capillaries. Extraction conditions: 11 cm×0.25 mm i.d. microextraction capillary; extraction time, 45 min (gravity fed at room temperature). Other conditions: 15 m×0.25 mm i.d. Restek Crossbond 14% cyanopropylphenyl-86% PDMS coated GC column; splitless desorption; injector temperature was 280° C.; programmed temperature GC run from 35° C. (1 min) to 270° C. at a rate of 20° C./min; helium carrier gas: FID 350° C. Peaks: (1) decanol, (2) hexanophenone, and (3) phenanthrene for all chromatograms.
Figure 11:
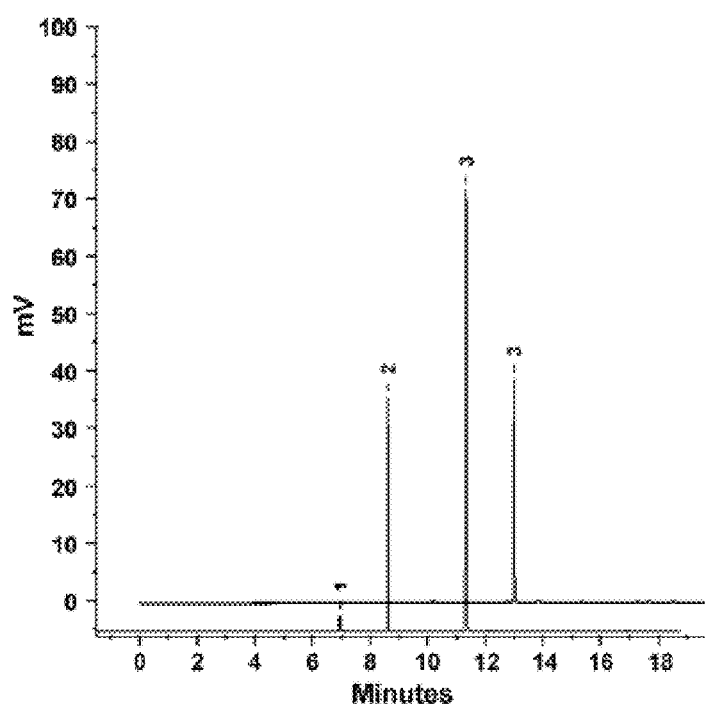
FIG. 11 is a composite graph comparing the CME-GC analysis of 500 ppb decanol, 500 ppb hexanophenone, and 200 ppb phenanthrene on (bottom plot) MOIC-mediated sol-gel PDMDPS and (top plot) sol-gel PDMDPS-no IL microextraction capillaries. Extraction conditions: 11 cm×0.25 mm i.d. microextraction capillary; extraction time, 45 min (gravity fed at room temperature). Other conditions: 15 m×0.25 mm i.d. Restek Crossbond 14% cyanopropylphenyl-86% PDMS coated GC column; splitless desorption; injector temperature was 300° C.; programmed temperature GC run from 35° C. (1 min) to 270° C. at a rate of 20° C./min; helium carrier gas: FID 350° C. Peaks: (1) decanol, (2) hexanophenone, and (3) phenanthrene for all chromatograms.

Extraction of an aqueous sample containing 500 ppb decanol, 500 ppb hexanophenone, and 200 ppb phenanthrene was performed on microextraction capillaries with different ionic liquid-mediated sol-gel coatings (TTPT-mediated BMPO, MOIC-mediated BMPO, and MOIC-mediated PDMDPS). For comparison, the same extraction experiments were performed on sol-gel capillaries prepared without the mediation of ILs (BMPO-no IL and PDMDPS-no IL). The MOIC-mediated sol-gel BMPO coating, seen in FIG. 10(A), and TTPT-mediated sol-gel BMPO coating, seen in FIG. 10(B), were both able to provide more efficient extractions than the BMPO-no IL sol-gel coating, seen in FIG. 10(C). Likewise, the MOIC-mediated sol-gel PDMDPS coating, seen in FIG. 11 bottom plot, provided a superior extraction performance compared to the PDMDPS-no IL coating, seen in FIG. 11 top plot. Clearly, the ILs had an explicit effect on the extraction capability of the prepared sol-gel sorbents. Both non-polar (PDMDPS) and moderately polar (BMPO) sol-gel sorbent coatings can be prepared following the described procedure. However, in the case of BMPO-based sol-gels, the MOIC-mediated sol-gel BMPO coated capillary, seen in FIG. 10(A), provided better extraction performance than TTPT-mediated sol-gel BMPO coated capillary, seen in FIG. 10(B). The MOIC-mediated sol-gel BMPO coated microextraction capillary provided enhanced GC peak areas, and the enhancement factors were 1.5 for decanol, 2.3 for hexanophenone, and 2.1 for phenanthrene.

Figure 12:
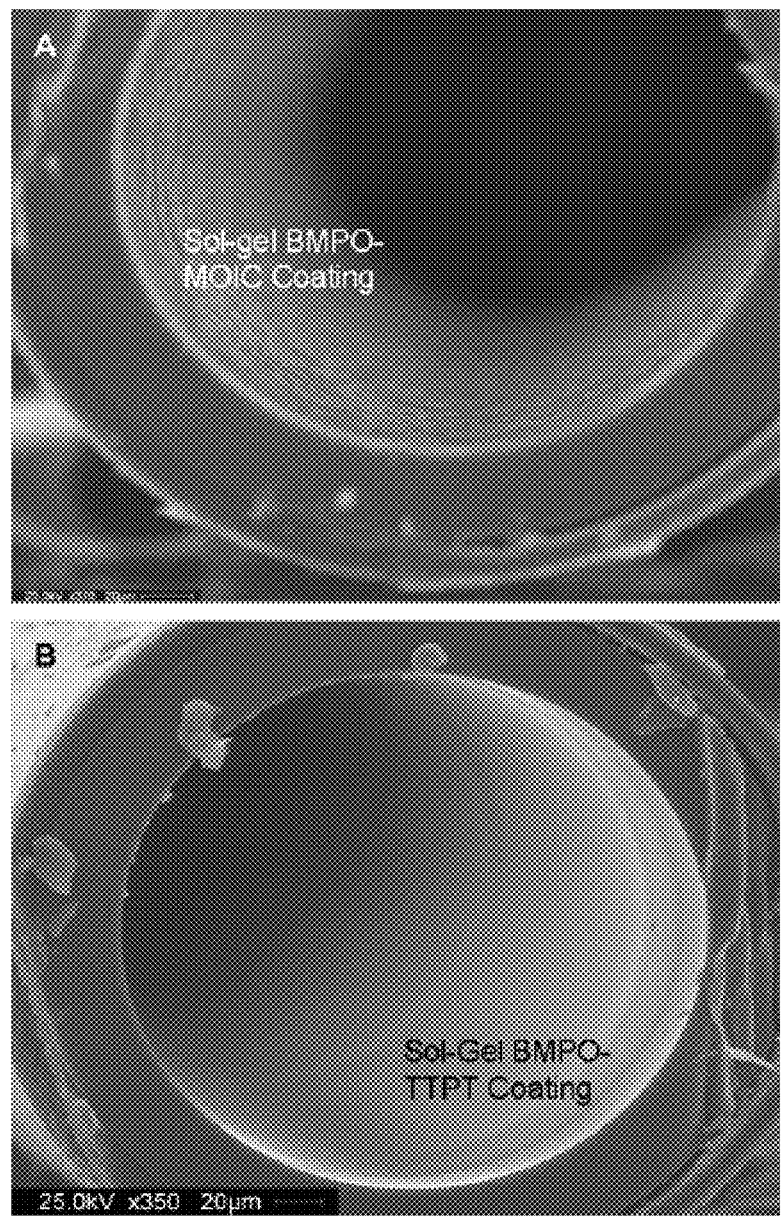
FIGS. 12(A) and (B) are scanning electron microscopic images of cross-sections of 250 µm i.d. (A) MOIC-mediated sol-gel BMPO (370×) and (B) TTPT-mediated sol-gel BMPO (350×) coated microextraction capillaries

ILs are known to act as porogens in sol-gel systems (Adams, et al., Aust. J. Chem. 54 (2001) 679; Zhou, e al., Nano Lett. 4 (2004) 477; Liu, et al., J. Chen, Anal. Chim. Acta 604 (2007) 107; Karout & Pierre, J. Non-Cryst. Solids 353 (2007) 2900; Wang, et al., Electrophoresis 29 (2008) 952; He, et al., Talanta 74 (2008) 1126; Zhang, et al., Microporous Mesoporous Mater. 119 (2009) 97; Donato, et al., J. Sol-Gel Sci. Technol. 49 (2009) 71). Thus, the IL-mediated sol-gel coatings provided enhanced GC peak areas because they were more porous than the non-IL-mediated BMPO sol-gel. Furthermore, SEM investigation of the morphology of the two BMPO sol-gel coatings revealed that the MOIC-mediated sol-gel BMPO coating, seen in FIG. 12(A), had a more porous morphology than the TTPT-mediated sol-gel BMPO coating, seen in FIG. 12(B). Enhanced GC peak areas provided by the MOIC-mediated sol-gel BMPO coating is indicative of a higher surface area of this coating compared to the TTPT mediated sol-gel BMPO coating. It has been pointed out (Adams, et al., Aust. J. Chem. 54 (2001) 679), that ILs with the same cation but different anions could have different effects on the porosity of mesoporous silica materials. It has also been noted that pore size of silica gel can be affected by variations of ILs (Zhang, et al., Microporous Mesoporous Mater. 119 (2009) 97). Therefore, it is logical to assume that the structural differences of the ionic liquids, seen in Table 1, likely resulted in varying effects on porosity of the sol-gel BMPO material. Many ILs represent green solvents (Forsyth, et al., Aust. J. Chem. 57 (2004) 113) and have been used by separation scientists as chromatographic stationary phases (Armstrong, et al., Anal. Chem. 71 (1999) 3873; Anderson, in: M. Koel (Ed.), Ionic Liquids in Chemical Analysis, CRC Press, Boca Raton, Fla., 2009, p. 139) and as extraction solvents (Huddleston, et al., Chem. Commun. 16 (1998) 1765). One important question that naturally arises is what role (if any) is played by the ionic liquids in the CME extraction process using sol-gel coatings prepared with the mediation of an IL (MOIC or TTPT). The answer becomes evident by looking into the decomposition temperatures of the used ILs. The decomposition for both of these ILs takes place at 190° C. (Merck, Ionic Liquids: New Materials for New Applications, Merck KGaA, Darmstadt, Germany, 2009); Chan, et al., Aust. J. Chem. 30 (1977) 2005). Since the CME capillaries were thermally conditioned above decomposition temperatures of these ILs (conditioning temperatures for sol-gel BMPO and PDMDPS were 280° C. and 300° C., respectively), it is safe to assume that the ILs had decomposed and the decomposition products had been carried away from the capillary by the purging flow of helium. Following this purging, the capillaries were rinsed with a mixture of 1:1 (v/v) $CH_2Cl_2$ and $CH_3OH$ and dried prior to use to ensure that any debris formed on the surface of the sol-gel coating during heating as well as un-bonded chemicals was removed. Thus, it is logical to assert that the used ILs did not participate in the extraction process and that extraction of analytes from the sample matrix occurred by interaction with the organic-inorganic hybrid sol-gel coating.

Figure 13:
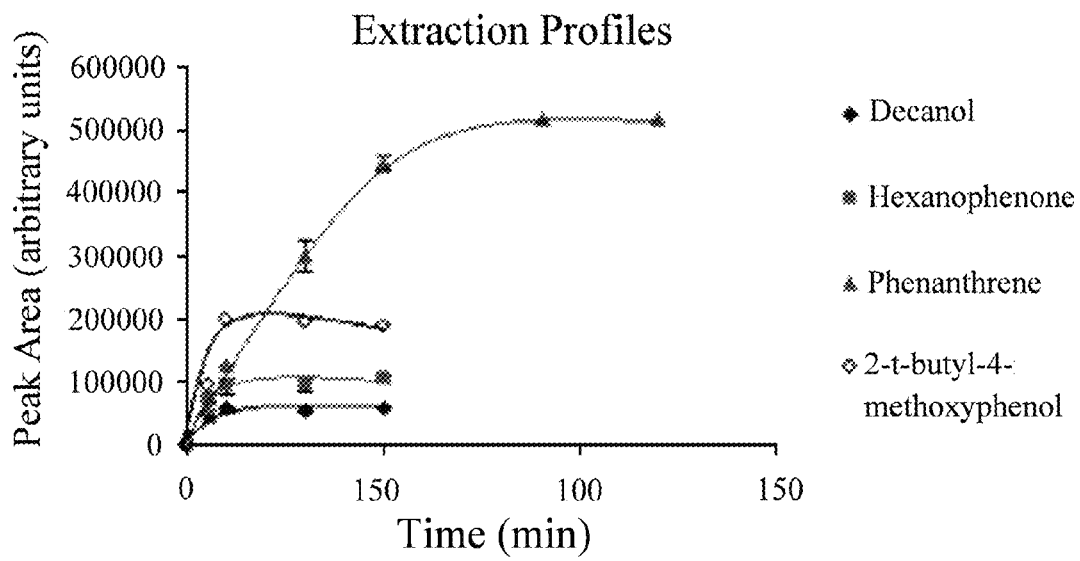
FIG. 13 is an extraction profile for a mixture of decanol, hexanophenone, and phenanthrene extracted on 11 cm×0.25 mm i.d. MOIC-mediated sol-gel BMPO microextraction capillary from an aqueous sample. Extraction conditions: triplicate extraction at various time intervals. GC analysis conditions: 15 m×0.25 mm i.d. Restek Crossbond 14% cyanopropylphenyl-86% PDMS coated GC column; splitless desorption; injector temperature was 280° C.; programmed temperature GC run from 35° C. (1 min) to 270° C. at a rate of 20° C./min; helium carrier gas: FID 350° C.

Since the MOIC-mediated sol-gel BMPO coated microextraction capillary provided the best extraction performance out of all of the prepared sol-gel coatings, these sol-gel coatings were further investigated. FIG. 13 illustrates the extraction profiles of 2-tert-butyl-4-methoxyphenol, decanol, hexanophenone, and phenanthrene on the MOIC-mediated sol-gel BMPO microextraction capillary. This IL-mediated sol-gel coating provided a fast equilibrium time (5-10 min) for relatively polar compounds like 2-tert-butyl-4-methoxyphenol, decanol, and hexanophenone and a slower equilibrium time (60-70 min) for nonpolar analytes like phenanthrene. It is likely that size of the pores in the sorbent does not have a great effect on the mass transfer of the PAHs into and out of the sorbent. Other investigators have demonstrated that pore size in sol-gels are in the nm range when ILs such as 1-butyl-3methylimidazolium tetrafluoroborate (Zhou, et al., Nano Lett. 4 (2004) 477; Karout & Pierre, J. Non-Cryst. Solids 353 (2007) 2900), 1-butyl-3methylimidazolium chloride (Klingshirn, et al., J. Mater. Chem. 15 (2005) 5174), and 1-butyl-3-metylpyridinium tetrafluoroborate (Karout & Pierre, J. Non-Cryst. Solids 353 (2007) 2900) are utilized as additives in the system. The calculated van derWaals diameter of phenanthrene according to Bondi (Bondi, J. Phys. Chem. 68 (1964) 441) is 7.24 Å and that of 2-tent-butyl-4-methoxyphenol is 7.16 Å. Since the PAH and the phenol have a very similar size it is likely that steric hindrance is not a major factor in the equilibrium kinetics. If this were the case then both the nonpolar phenanthrene and the polar 2-tent-butyl-4-methoxyphenol would have had slow equilibrium kinetics. This is not observed in the experimental data, seen in FIG. 13. The slow equilibrium kinetics for the PAHs is likely a result of the lower affinity of this type of nonpolar molecule for the polar sol-gel sorbent. From a practicality perspective, this is an important, highly desirable result, considering the difficulties associated with the extraction of polar analytes from aqueous matrices (Fontanals, et al., J. Chromatogr. A 1152 (2007) 14).

Figure 14:
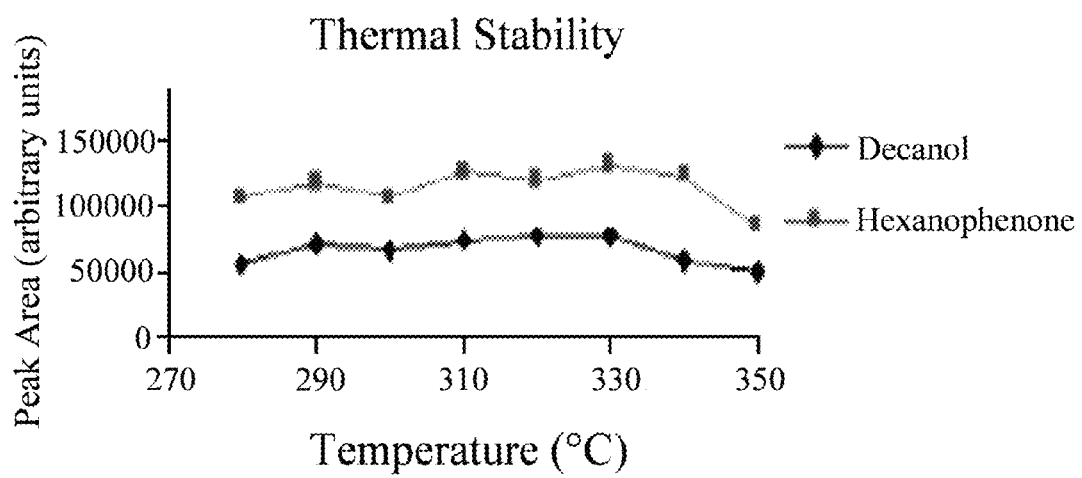
FIG. 14 is a graph showing the effect of conditioning temperature on the performance of MOIC-mediated sol-gel BMPO microextraction capillary. CME-GC conditions: extraction time, 45 min; 15 m×0.25 mm i.d. Restek Crossbond 14% cyanopropylphenyl-86% PDMS coated GC column; splitless injection; injector: initial 40° C., final (mentioned on x-axis), programmed at a rate of 60° C./min; GC over temperature programmed temperature from 35° C. (1 min) to 270° C. at a rate of 20° C./min; helium carrier gas: FID 350° C.

The thermal stability of the MOIC-mediated sol-gel BMPO microextraction coating was evaluated by conditioning the coated capillary stepwise at higher temperatures and performing extractions on the capillary after every conditioning step. The MOIC-mediated sol-gel BMPO capillary was thermally conditioned stepwise for 1 h each at 280° C., 290° C., 300° C., 310° C., 320° C., 330° C., 340° C., and 350° C. in a GC oven purging the capillary with helium (1 mL min). The GC peak areas of the extracted analytes (decanol and hexanophenone) remained practically constant in this conditioning process until 330° C. A slight drop in GC peak area for the analytes was observed at conditioning temperatures exceeding 330° C., seen in FIG. 14, indicating that the coating was stable at least up to 330° C. The reduction in GC peak area can be attributed to a change in the extraction performance of the BMPO polymer due to the onset of thermal degradation. BMPO is a relatively low molecular weight (500-900 g mol) polyalkylene oxide material that demonstrated this remarkable thermal stability when used in the IL-mediated sol-gel. By comparison, conventionally prepared coatings for a polyalkylene oxide (e.g. PEG, Ucon, etc.) of similar molecular weight is unlikely to exceed 200-250° C. (Castello &. D'Amato, J. Chromatogr. 90 (1974) 291). The excellent thermal stability is due to the strong chemical bonding between the MOIC-mediated sol-gel BMPO coating and the inner walls of the fused silica capillary.

The sol-gel coating's extraction ability was investigated using nonpolar (PAHs), moderately polar (aliphatic aldehydes and aromatic ketones), seen in Table 5, and polar (aliphatic alcohols, aromatic amines, phenols, and free fatty acids), seen in Table 6, test solutes. For all of the studied analytes, run-to-run GC peak area relative standard deviation (RDS) values were determined to evaluate the repeatability of CME with the MOIC-mediated sol-gel BMPO coating. GC peak area RSD values ranged from 0.4% to 5.7% for the nonpolar moderately polar compounds. The RSD values ranged from 0.3% to 6.7% for the polar analytes. These reasonably small RSD values translate into excellent repeatability in CME performance of the MOIC-mediated sol-gel BMPO coating for the classes of compounds investigated. This coating provided ng L detection limits for all the analytes—polar, nonpolar, and moderately polar. Furthermore, the sol-gel coating was solvent resistant since it was used in all extraction experiments after it had been rinsed with organic solvents.

TABLE 5

Run-to-run repeatability (peak area) and detection limit data for nonpolar and moderately polar analytes in three replicate measurements by CME-GC using sol-gel BMPO-MOIC coated microextraction capillaries.

| Chemical class | Name of analyte | Mean peak area (arbitrary unit) | RSD (%) | Detection limit S/N = 3 (ng/L) |
|---|---|---|---|---|
| PAH | Acenaphthene | 77.5 | 1.8 | 11.6 |
| | Phenanthrene | 395.3 | 5.7 | 2.3 |
| | Pyrene | 232.8 | 4.5 | 1.9 |
| Ketone | Hexanophenone | 93.0 | 2.6 | 24.2 |
| | Heptanophenone | 176.4 | 2.4 | 12.8 |
| | Decanophenone | 216.2 | 4.5 | 6.2 |
| Aldehyde | Decanal | 39.2 | 0.4 | 69.0 |
| | Undecanal | 55.3 | 3.2 | 40.6 |
| | Dodecanal | 114.7 | 2.3 | 19.6 |

TABLE 6

Run-to-run repeatability (peak area) and detection limit data for polar and moderately polar analytes in three replicate measurements by CME-GC using sol-gel BMPO-MOIC coated microextraction capillaries

| Chemical class | Name of analyte | Mean peak area (arbitrary unit) | RSD (%) | Detection limit S/N = 3 (ng/L) |
|---|---|---|---|---|
| Alcohol | Nonanol | 59.9 | 6.6 | 60.1 |
| | Decanol | 53.8 | 1.7 | 41.8 |
| | Undecanol | 182.8 | 6.7 | 12.3 |
| Aromatic amine | N-Butylaniline | 32.8 | 5.9 | 109.8 |
| | Acridine | 116.0 | 2.6 | 31.0 |
| | Diphenylamine | 188.0 | 0.3 | 19.1 |
| Phenol | 2,4,6-Trichlorophenol | 23.5 | 2.2 | 153.3 |
| | 2-tert-Butyl-4-methoxyphenol | 39.7 | 4.3 | 90.7 |
| | Pentachlorophenol | 55.1 | 0.3 | 65.3 |
| Acid | Nonanoic acid | 10.9 | 5.0 | 330.5 |
| | Decanoic acid | 32.6 | 4.0 | 110.3 |
| | Undecanoic acid | 111.3 | 3.1 | 32.4 |

Capillary-to-capillary RSD values in GC peak areas of extracted analytes (which is a measure of reproducibility of the coating procedure) was determined by obtaining GC peak area values for decanol, hexanophonone, and phenanthrene extracted on three individually prepared MOIC-mediated sol-gel BMPO microextraction capillaries. The capillary-to-capillary GC peak areas obtained provided RDS values of 7.2% for decanol, 8.6% for hexanophenone, and 3.9% for phenanthrene. These RSD values are indicative of acceptable reproducibility of the used sol-gel coating procedure.

IL-mediated sol-gel PDMS and BMPO coatings were developed for use as immobilized sorbents in capillary microextraction. Ionic liquid-mediated sol-gel PDMS coatings provided consistent performance in CME-GC analysis (run-to-run peak area RSD values of 4.2-5.0%) compared with sol-gel PDMS coatings prepared without ionic liquid (2.8-14.1%). PDMS and BMPO IL-mediated sol-gel coatings also provided lower detection limits, compared to analogous sol-gel coatings prepared without IL. Scanning electron microscopy results suggest that ILs can provide a porous morphology of sol-gel extraction media when it is incorporated in the sol-gel coating solution.

The MOIC-mediated sol-gel BMPO coating provided superior preconcentration performance than TTPT-mediated sol-gel BMPO coating. SEM investigations revealed that the use of MOIC in the sol-gel system resulted in a more porous morphology responsible for a more efficient extraction performance. The MOIC-mediated sol-gel BMPO coating provided consistent extraction results in CME-GC analysis (run-to-run peak area RSD values ranged from 0.3% to 6.7%) for nonpolar and polar analytes.

Enhancement of porosity alone was not enough to provide effective extraction of analytes. Thus, careful choice of the polymer and precursor with comparable sol-gel reactivity must be made when designing an IL-mediated sol-gel sorbent in order to ensure that the created sol-gel coating inherently possesses the desired sorbent characteristics. IL-mediated sol-gel materials hold great potential for being widely used as sorbents and stationary phases in separation science.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosure of all publications cited above are expressly incorporated herein by reference, each in its entirety, to the same extent as if each were incorporated by reference individually.

While there has been described and illustrated specific embodiments from the foregoing description, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween

What is claimed is:

1. An extraction column, comprising
   a column having a wall, wherein the wall has a substantially circular perimeter;
   a continuous porous coating disposed on the inner face of the wall, wherein the coating is made from the steps:
   obtaining a first sol-gel precursor, wherein the first precursor is hydroxy-terminated poly(dimethylsiloxane), bis[(3-methyldimethoxysilyl)-propyl]polypropylene oxide, poly(tetrahydrofuran) 250, poly(ethylene glycol) MW 600, poly(dimethylsiloxane-co-diphenylsiloxane), dihydroxyterminated, or a derivative thereof;
   adding an ionic liquid to the first sol-gel precursor to form a precursor-ionic liquid mixture, wherein the ionic liquid is a phosphonium-based ionic liquid, imidazolium-based ionic liquid, pyridinium-based ionic liquid, or a combination thereof;
   mixing a second sol-gel precursor into the precursor-ionic liquid mixture, wherein the second sol-gel precursor is an alkoxy compound of an element M, where M is silicon, titanium, zirconium, germanium, vanadium, zinc, tantalum, niobium, tungsten; and
   mixing a catalyst into the precursor-ionic liquid mixture to form a sol-gel mixture, wherein the catalyst is an acid, base, or fluoride compound.

2. The extraction column of claim 1, wherein the alkoxy compound is tetramethoxysilane, tetraethoxysilane, tetrapropoxysilane, tetraisopropoxysilane, or tetrabutoxysilane.

3. The extraction column of claim 1, wherein the ionic liquid is trihexyltetradecylphosphonium tetrafluoroborate, 1-methyl-3-octylimidazolium chloride, or 4-methyl-N-butylpyridinium tetrafluoroborate.

4. The extraction column of claim 1, wherein the catalyst is an organic acid or inorganic acid.

5. The extraction column of claim 4, wherein the catalyst has a pKa of less than 4.

6. The extraction column of claim 5, wherein the coating is made from the additional step of adding a solvent prior to the addition of the second sol-gel precursor, wherein the solvent is methylene chloride, methanol, ethanol, tetrahydrofuran, or a combination thereof.

7. The extraction column of claim 1, wherein the catalyst is trifluoroacetic acid.

8. The extraction column of claim 1, wherein the coating is made from the additional step of conditioning the extraction column, comprising the steps of
   placing the extraction column in a gas chromatograph oven;
   passing helium gas along the exterior surface of the coating;
   elevating the temperature of the gas chromatograph oven at until the oven reaches a conditioning temperature;
   where the conditioning temperature is 400° C. or below.

* * * * *

UNITED STATES PATENT AND TRADEMARK OFFICE
CERTIFICATE OF CORRECTION

PATENT NO. : 8,623,279 B2
APPLICATION NO. : 13/300943
DATED : January 7, 2014
INVENTOR(S) : Abdul Malik and Anne M. Shearrow It is certified that error appears in the above-identified patent and that said Letters Patent is hereby corrected as shown below:

In the Specification

Column 1, lines 15-19 should read

This invention was made with government support under Grant # DGE 0221681 awarded by the National Science Foundation, and Grant # DE-AC05-00OR22750 awarded by the Department of Energy. The government has certain rights in the invention.

Signed and Sealed this
Third Day of June, 2014

Michelle K. Lee
*Deputy Director of the United States Patent and Trademark Office*